US008512949B2

(12) United States Patent
Zama et al.

(10) Patent No.: US 8,512,949 B2
(45) Date of Patent: Aug. 20, 2013

(54) DIAGNOSIS/TREATMENT OPTION FOR HEAD-AND-NECK TUMOR USING MICRO-RNA AS BIOMARKER

(75) Inventors: Takeru Zama, Tokyo (JP); Koichiro Saito, Tokyo (JP); Akira Hirasawa, Tokyo (JP); Hideki Naganishi, Tokyo (JP)

(73) Assignees: Takeru Zama, Tokyo (JP); Koichiro Saito, Tokyo (JP)

( * ) Notice: Subject to any disclaimer, the term of this patent is extended or adjusted under 35 U.S.C. 154(b) by 0 days.

(21) Appl. No.: 12/996,420

(22) PCT Filed: Jun. 10, 2009

(86) PCT No.: PCT/JP2009/002629
§ 371 (c)(1),
(2), (4) Date: Feb. 17, 2011

(87) PCT Pub. No.: WO2009/150839
PCT Pub. Date: Dec. 17, 2009

(65) Prior Publication Data
US 2011/0143950 A1    Jun. 16, 2011

(30) Foreign Application Priority Data

Jun. 12, 2008 (JP) ................................ 2008-154547
Sep. 22, 2008 (JP) ................................ 2008-243306
Apr. 16, 2009 (JP) ................................ 2009-099849

(51) Int. Cl.
*C12Q 1/68* (2006.01)

(52) U.S. Cl.
USPC .......................................... 435/6.1; 435/6.11

(58) Field of Classification Search
None
See application file for complete search history.

(56) References Cited

U.S. PATENT DOCUMENTS

| 6,855,350 B2 | 2/2005 | Lu |
| 7,045,292 B2 | 5/2006 | Mai |

FOREIGN PATENT DOCUMENTS

| JP | 2005-532314 | 10/2005 |
| JP | 2007-00052 | 1/2007 |
| JP | 2007-502990 | 2/2007 |
| WO | WO 2008/036776 | 3/2008 |
| WO | WO 2008/073923 | 6/2008 |

OTHER PUBLICATIONS

Mandrekar et al., Clinical trial designs for predictive biomarker validation: one size does not fit all; J Biopharmaceutical Statistics, vol. 19, pp. 530-542, 2009.*
Paik, Molecular profiling of breast cancer; Curr Opin Obstet Gynecol vol. 18, pp. 59-63, 2006.*
Feber et al., MicroRNA expression profiles of esophageal cancer; Journal of thoracic and Cardiovascular Surgery, vol. 135, No. 2, pp. 255-260, 2008.*
NCBI Gene Expression Omnibus accession No. GPL9173 screen capture, accessed Jun. 8, 2012.*
Debernardi et al., MicroRNA miR-181a correlates with morphological sub-class of acute myeloid leukaemia and the expression of its target genes in global genome-wide analysis; Leukemia, vol. 21, pp. 912-916, 2007.*
Liu et al., Combination of plasma microRNAs with serum CA19-9 for early detection of pancreatic cancer; International Journal of Cancer, vol. 131, pp. 683-691, 2012.*
Argiris et al., "Head and Neck Cancer," The Lancet, pp. 1695-1709, May 2008.
Barbarotto et al., "MicroRNAs and Cancer: Profile, Profile, Profile," Int. J. Cancer, 122, pp. 969-977, 2008.
Chang et al., "MicroRNA Alterations in Head and Neck Squamous Cell Carcinoma," Int. J. Cancer, 123, pp. 2791-2797, 2008.
Hashibe et al., "Alcohol Drinking in Never Users of Tobacco, Cigarette Smoking in Never Drinkers, and the Risk of Head and Neck Cancer: Pooled Analysis in the International Head and Neck Cancer Epidemiology Consortium," J. Natl. Cancer Inst., 100(3), pp. 777-789, 2008.
He et al., "The Role of MicroRNA Genes in Papillary Thyroid Carcinoma," PNAS, 102(52), pp. 19075-19080, Dec. 2005.
Hoogsteen et al., "Tumor Microenvironment in Head and Neck Squamous Cell Carcinomas: Predictive Value and Clinical Relevance of Hypoxic Markers. A Review," Head and Neck, 29(6), pp. 591-604, Jun. 2007.
Jiang et al., Real-Time Expression Profiling of MicroRNA Precursors in Human Cancer Cell Lines, Nucleic Acids Research, 33(17), pp. 5394-5403, 2005.
Lothaire et al., "Molecular Markers of Head and Neck Squamous Cell Carcinoma: Promising Signs in Need of Prospective Evaluation," Head and Neck, 28(3), pp. 256-269, Mar. 2006.
Marsh et al., "Cancer Pharmcogenetics," Methods Mol. Biol., 448, Chapter 15, pp. 437-446, 2008.
Marur et al., "Head and Neck Cancer: Changing Epidemiology, Diagnosis, and Treatment," Mayo Clin. Proc., 83(4), pp. 489-501, 2008.
Tran et al., "MicroRNA Expression Profiles in Head and Neck Cancer Cell lines," Biochemical and Biophysical Research Communications, 358, pp. 12-17, 2007.
Zama, "Cancer Studies Change with MicroDNA Focused on Head-and-Neck Tumor and Gynecological Tumor," The 50th Annual Meeting of the Japanese Society of Oral Biology, Sep. 10, 2008, p. 108.
Zeng et al., "MicroRNAs and Small Interfering RNAs Can inhibit mRNA Expression by Similar Mechanisms," PNAS, 100(17), pp. 9779-9784, 2003.
Zhang et al., "MicroRNAs as Oncogenes and Tumor Suppressor," Developmental Biology, 302, pp. 1-12, 2007.

* cited by examiner

*Primary Examiner* — Celine Qian
*Assistant Examiner* — Addison D Ault
(74) *Attorney, Agent, or Firm* — Kenneth H. Sonnenfeld; Margaret B. Brivanlou; King & Spalding LLP

(57) ABSTRACT

Disclosed are: a method for using a particular microRNA as a biomarker for head-and-neck tumor; a method for the determination of head-and-neck tumor; a kit for the determination of head-and-neck tumor, and the like. The present invention is characterized in that at least one microRNA selected from the group of microRNAs consisting of miR-455-3p, miR-455-5p, miR-130b, miR-130b*, miR-801, miR-196a, miR-21, miR-31, miR-133b, miR-145 and miR-375 is used as a biomarker for head-and-neck tumor.

5 Claims, 14 Drawing Sheets

Figure 1

SAMPLES

| SAMPLE ID | SAMPLES | TISSUES |
|---|---|---|
| 1 | NORMAL1 | LARYNX |
| 2 | NORMAL2 | LARYNX |
| 3 | POLYP | VOCAL CORD |
| 4 | MODERATE DYSPLASIA | LARYNX |
| 5 | SEVERE DYSPLASIA | LARYNX |
| 6 | CANCER1 | LARYNX |
| 7 | CANCER2 | LARYNX |
| 8 | CANCER 3 (RECURRENCE) | LARYNX |

Figure 2

QUALITY EXAMINATION OF TOTAL RNA BY SAMPLE UV-VIS

| SAMPLE ID | CONCENTRATION (ng/uL) | OD 260/280 | OD 260/230 |
|---|---|---|---|
| 1 | 29.73 | 1.91 | 1.83 |
| 2 | 29.7 | 1.9 | 1.62 |
| 3 | 30.67 | 1.86 | 1.27 |
| 4 | 30.11 | 1.89 | 1.35 |
| 5 | 30.56 | 1.95 | 1.71 |
| 6 | 30.56 | 1.78 | 2.12 |
| 7 | 30.52 | 1.81 | 1.95 |
| 8 | 29.39 | 1.86 | 1.47 |

DILUTION TO 30 ng/μL

START LABELING AT 100 ng OF TOTAL RNA

QUALITY CHECKING OF TOTAL RNA BY BIO-ANALYZER RNA6000 NANO ASSAY

MicroRNA WHOSE EXPRESSION INCREASES FOR LARYNGEAL CANCER

Figure 6
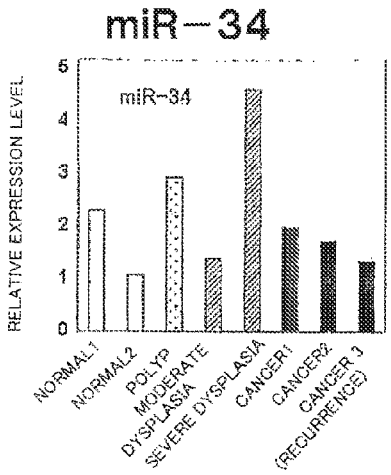
Figure 7 let-7 FAMILY
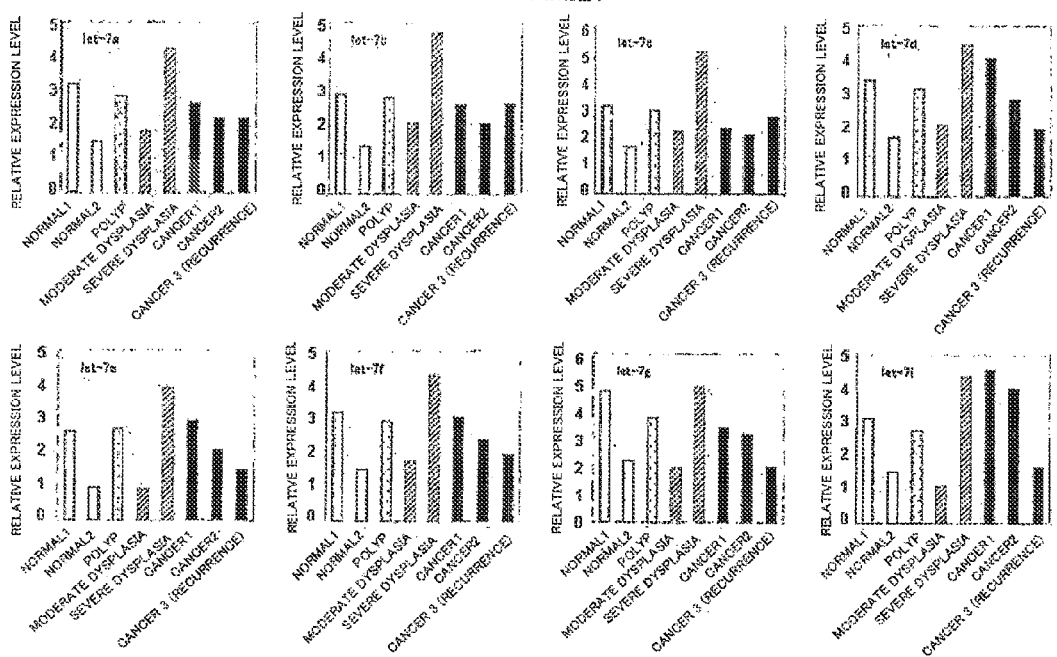

DIAGNOSIS/TREATMENT OPTION FOR HEAD-AND-NECK TUMOR USING MICRO-RNA AS BIOMARKER

TECHNICAL FIELD

The present invention relates to an expression profile of a microRNA (miRNA) in head-and-neck tumor and a use thereof. More specifically, the present invention relates to a method for using a specific microRNA as a biomarker for the head-and-neck tumor, a method for the determination of the head-and-neck tumor, a kit for the determination of the head-and-neck tumor, and the like.

BACKGROUND ART

Head-and-neck tumor is a tumor formed in the ear, nose, pharynx, larynx, cervix, facial surface, oral cavity, or the like; particularly, a malignant one is prevalent in men 50 years old or more and accounts for 6% of all malignant tumors. The incidence rate thereof increases with increasing age; 650,000 people are annually affected thereby in the whole world and of these, 350,000 die of the malignant tumor (see Non-Patent Document 1). Among others, laryngeal cancer is the most common disease in the head and neck area; the number of fatalities is estimated to increase according to the future prediction of the annual death number due to the laryngeal cancer by the Cancer Statistics White Paper.

The diagnosis of head-and-neck tumor is performed by staging using endoscopy and various imaging tests (CT, MRI, PET, ultrasonography, etc.) and tissue diagnosis by biopsy, and treatment is carried out based thereon (see Non-Patent Document 2). However, for the diagnosis of head-and-neck tumor, the imaging tests cannot qualitatively diagnose the tumor and in many instances make it difficult to differentiate the tumor from benign disease. The tissue diagnosis by biopsy, which is used as a definite diagnosis, also sometimes makes the determination of progression and invasion degrees of the tumor difficult as well as at present not enabling the prediction of prognosis thereof even when the basic hematoxylin-eosin (HE) stain is used in combination with various immunostainings. Although several factors for prediction of onset and prognosis of the tumor are reported (Patent Documents 1 to 3), there currently exists no biomarker sufficient in both sensitivity and specificity.

Treatment of head-and-neck tumor is determined depending primarily on the disease stage and histopathological manifestation thereof; while radical single-stage extirpation is carried out for benign tumor, surgery, radiotherapy and chemotherapy are used for malignant tumor and the combination thereof is required to be performed for advanced cancer. Surgery for head-and-neck tumor prominently damages the head-and-neck and the face surface cosmetically as well as highly affecting physical functions such as phonation and deglutition and therefore is highly invasive physically and psychologically, so that it causes a substantial reduction in QOL (quality of life). Even the combination of these treatments also makes the 5-year survival rate remain on the order of 30% for advanced cancer (see Non-Patent Document 2), and its therapeutic effect can never be said even now to be high. In addition, there are observed individual variations in therapeutic effect and prognosis, which are probably due to mutated gene and its abnormal expression level in tumor tissue (see Non-Patent Documents 3 and 4); however, to date the diagnosis of head-and-neck tumor at the gene level has not been carried out.

As described above, an increase in head-and-neck tumor is predicted in Japan, which is reaching an aging society; however, for prediction of onset thereof, to date no useful biomarker has been found (see Patent Documents 4 and 5 and Non-Patent Document 6) although an association of the onset with smoking, drinking, backflow of stomach acid, or overuse of voice is epidemiologically suggested (Non-Patent Document 5).

Meanwhile, a microRNA is a single-stranded RNA which is present in cells, not translated into protein, and on the order of 22 bases long (see Non-Patent Document 7). It was discovered in *C. elegans* in 1993 and thereafter also in a vertebrate in 2001 and is conserved beyond species. Currently, about 1,000 microRNAs are predicted to be present on the human genome; 700 or more of microRNAs have so far been cloned. MicroRNAs are believed to control genes in 30% of protein-coding regions on the genome (see Non-Patent Document 8); therefore, the functional failure of microRNAs has a possibility of causing various diseases. However, to date a very few microRNAs have biological roles elucidated; future analysis is awaited. Reports of microRNAs for head-and-neck tumor are found here and there in the case of using tumor cell lines (see Non-Patent Documents 9 and 10); however, up to date no report in which a patient's clinical specimen is used is found.

CITATION LIST

Patent Document

Patent Document 1: Japanese Patent Laid-Open No. 2005-532314
Patent Document 2: U.S. Pat. No. 6,855,350
Patent Document 3: U.S. Pat. No. 7,045,292
Patent Document 4: Japanese Patent Laid-Open No. 2007-000052
Patent Document 5: National Publication of International Patent Application No. 2007-502990

Non-Patent Document

Non-Patent Document 1: Argiris A, Karamouzis M V, Raben D, Ferris R L. Head and neck cancer. Lancet. 2008; 371 (9625): 1695-1709.
Non-Patent Document 2: Marur S, Forastiere A A. Head and neck cancer: changing epidemiology, diagnosis, and treatment. Mayo Clin Proc. 2008; 83(4): 489-501.
Non-Patent Document 3: Marsh S. Cancer pharmacogenetics. Methods Mol. Biol. 2008; 448: 437-46.
Non-Patent Document 4: Lothaire P, de Azambuja E, Dequanter D, Lalami Y, Sotiriou C, Andry G, Castro G Jr, Awada A. Molecular markers of head and neck squamous cell carcinoma: promising signs in need of prospective evaluation. Head Neck. 2006; 28(3): 256-69.
Non-Patent Document 5: Hashibe M, Brennan P, Benhamou S, Castellsague X, Chen C, Curado M P, Dal Maso L, Daudt A W, Fabianova E, Fernandez L, Wunsch-Filho V, Franceschi S, Hayes R B, Herrero R, Koifman S, LaVecchia C, Lazarus P, Levi F, Mates D, Matos E, Menezes A, Muscat J, Eluf-Neto J, Olshan A F, Rudnai P, Schwartz S M, Smith E, Sturgis E M, Szeszenia-Dabrowska N, Talamini R, Wei Q, Winn D M, Zaridze D, Zatonski W, Zhang Z F, Berthiller J, Boffetta P. Alcohol drinking in never users of tobacco, cigarette smoking in never drinkers, and the risk of head and neck cancer: pooled analysis in the International Head and Neck Cancer Epidemiology Consortium. J. Natl Cancer Inst. 2007; 99(10): 777-89. Erratum in: J. Natl Cancer Inst. 2008; 100(3): 225.

Non-Patent Document 6: Hoogsteen I J, Marres H A, Bussink J, vander Kogel A J, Kaanders J H. Tumor microenvironment in head and neck squamous cell carcinomas: predictive value and clinical relevance of hypoxic markers. Head Neck. 2007; 29 (6): 591-604.

Non-Patent Document 7: Barbarotto E, Schmittgen T D, Calin G A. microRNAs and cancer: profile, profile, profile. Int. J. Cancer. 2008; 122(5): 969-977.

Non-Patent Document 8: Zeng Y, Yi R, Cullen B R. miRNAs and small interfering RNAs can inhibit mRNA expression by similar mechanisms. Proc. Nat. Acad. Sci. 2003; 100: 9779-9784.

Non-Patent Document 9: Tran N, McLean T, Zhang X, Zhao C J, Thomson J M, O'Brien C, Rose B. microRNA expression profiles in head and neck cancer cell lines. Biochem. Biophys. Res. Commun. 2007; 358: 12-17.

Non-Patent Document 10: Jiang J, Lee E J, Gusev Y, Schmittgen T D, Real-time expression profiling of microRNA precursors in human cancer cell lines. Nucleic Acids Res. 2005; 33: 5394-5403.

DISCLOSURE OF THE INVENTION

Problems to be Solved by the Invention

An object of the present invention is to provide a method for using a specific microRNA as a biomarker for head-and-neck tumor, a method for the determination of head-and-neck tumor, a kit for the determination of head-and-neck tumor, and the like.

Means for Solving the Problems

As described above, reports of microRNAs for head-and-neck tumor are found here and there in the case of using tumor cell lines; however, up to date no report in which a patient's clinical specimen is used is found. A tumor cell line is known to have a different expression profile of gene and the like from the expression profile of a clinical specimen of tumor cells corresponding to the cell line because unlike a clinical specimen, the tumor cell line does not constitute a tissue, is not influenced by other biomolecules from other tissues, and the like. Thus, it is basically impossible to predict the expression profile of a clinical specimen from the expression profile of a cell line. Under such circumstances, the present inventors have compared microRNAs of laryngeal tumor tissue with microRNAs of laryngeal normal tissue and have found that a particular microRNA is abnormally expressed in the laryngeal tumor tissue, thereby accomplishing the present invention. The present inventors also collected blood samples before surgical removal of cancer and after a lapse of 30 days from such removal, in patients with laryngeal cancer as one of head-and-neck tumors (laryngeal cancer subjects) and measured the concentration of the particular microRNA in each blood sample. As a result, the present inventors have also found that among microRNAs whose expression increases compared to the control in the head-and-neck tumor tissue, the particular microRNA decreases after a lapse of 30 days from the surgery to a blood concentration of about 1/120 the blood concentration thereof before the surgical removal of cancer, thereby accomplishing the present invention.

Specifically, the present invention relates to (1) a method for using one or more microRNAs selected from the group of microRNAs consisting of miR-455-3p, miR-455-5p, miR-130b, miR-130b*, miR-801, miR-196a, miR-21, miR-31, miR-133b, miR-145 and miR-375 as a biomarker for head-and-neck tumor, (2) the method according to item (1) above, wherein the miR-455-3p, miR-455-5p, miR-130b, miR-130b*, miR-801, miR-196a, miR-21, miR-31, miR-133b, miR-145 and miR-375 are RNAs in which one or more nucleotides are deleted, substituted or added in the nucleotide sequences represented by SEQ ID NOs:1 to 11, respectively, and whose expression increases or decreases in a head-and-neck tumor tissue or blood of a head-and-neck tumor subject compared to a control, and (3) the method according to item (1) or (2) above, wherein the head-and-neck tumor is laryngeal cancer or squamous cell cancer.

The present invention also relates to (4) a method for the determination of head-and-neck tumor, comprising the steps of: (A) extracting RNA from a specimen tissue from the head and neck or blood of a subject; (B) measuring the expression level of one or more microRNAs selected from miR-455-3p, miR-455-5p, miR-130b, miR-130b*, miR-801, miR-196a, miR-21, miR-31, miR-133b, miR-145 and miR-375 in the extracted RNA; and (C) comparing the measured expression level to the expression level of the microRNAs in a normal tissue of the same type as that of the specimen tissue or in blood of a normal subject of the same species as that of the above subject as a control for evaluation, (5) the method for the determination of head-and-neck tumor according to item (4) above, wherein the miR-455-3p, miR-455-5p, miR-130b, miR-130b*, miR-801, miR-196a, miR-21, miR-31, miR-133b, miR-145 and miR-375 are RNAs in which one or more nucleotides are deleted, substituted or added in the nucleotide sequences represented by SEQ ID NOs:1 to 11, respectively and whose expression increases or decreases in the head-and-neck tumor tissue or the blood of the head-and-neck tumor subject compared to a control, (6) the method for the determination of head-and-neck tumor according to item (4) or (5) above, wherein the tumor is determined as being head-and-neck tumor when the expression level of one or more microRNAs selected from the group of microRNAs consisting of miR-455-3p, miR-455-5p, miR-130b, miR-130b*, miR-801, miR-196a, miR-21, and miR-31 in the extracted RNA increases compared to a control, (7) the method for the determination of head-and-neck tumor according to item (4) or (5) above, wherein the tumor is determined as being head-and-neck tumor when the expression level of one or more microRNAs selected from the group of microRNAs consisting of miR-133b, miR-145 and miR-375 in the extracted RNA decreases compared to a control, and (8) the method for the determination of head-and-neck tumor according to any one of items (4) to (7) above, wherein the head-and-neck tumor is laryngeal cancer or squamous cell cancer.

The present invention further relates to (9) a method of using for the determination of head-and-neck tumor a microarray which includes a polynucleotide consisting of a nucleic acid sequence complementary to the sequence of one or more microRNAs selected from the group of microRNAs consisting of miR-455-3p, miR-455-5p, miR-130b, miR-130b*, miR-801, miR-196a, miR-21, miR-31, miR-133b, miR-145 and miR-375 or a part thereof, and which is capable of measuring the expression level of the microRNA, (10) a method of using for the determination of head-and-neck tumor a primer set capable of amplifying the sequence of one or more microRNAs selected from the group of microRNAs consisting of miR-455-3p, miR-455-5p, miR-130b, miR-130b*, miR-801, miR-196a, miR-21, miR-31, miR-133b, miR-145 and miR-375 and a fluorescent probe comprising a polynucleotide consisting of a nucleic acid sequence complementary to the microRNA sequence or a part thereof, (11) the method according to item (9) or (10) above, wherein the miR-455-3p, miR-455-5p, miR-130b, miR-130b*, miR-801, miR-196a, miR-21, miR-31, miR-133b, miR-145 and miR-375 are RNAs in which one or more nucleotides are deleted, substituted or added in the nucleotide sequences represented by SEQ ID NOs:1 to 11, respectively and whose expression increases or decreases in head-and-neck tumor tissue or blood of a head-and-neck tumor subject compared to a control, and (12) the method according to anyone of items (9) to (11) above, wherein the head-and-neck tumor is laryngeal cancer or squamous cell cancer.

The present invention still further relates to (13) a kit for the determination of head-and-neck tumor, comprising a microarray which includes a polynucleotide consisting of a nucleic acid sequence complementary to the sequence of one or more microRNAs selected from the group of microRNAs consisting of miR-455-3p, miR-455-5p, miR-130b, miR-130b*, miR-801, miR-196a, miR-21, miR-31, miR-133b, miR-145 and miR-375 or a part thereof, and which is capable of measuring the expression level of the microRNA, (14) a kit for the determination of head-and-neck tumor, including a primer set capable of amplifying the sequence of one or more microRNAs selected from the group of microRNAs consisting of miR-455-3p, miR-455-5p, miR-130b, miR-130b*, miR-801, miR-196a, miR-21, miR-31, miR-133b, miR-145 and miR-375 and a fluorescent probe comprising a polynucleotide consisting of a nucleic acid sequence complementary to the microRNA sequence or a part thereof, and (15) the determination kit according to item (13) or (14) above, wherein the miR-455-3p, miR-455-5p, miR-130b, miR-130b*, miR-801, miR-196a, miR-21, miR-31, miR-133b, miR-145 and miR-375 are RNAs in which one or more nucleotides are deleted, substituted or added in the nucleotide sequences represented by SEQ ID NOs:1 to 11, respectively and whose expression increases or decreases in head-and-neck tumor tissue or blood of a head-and-neck tumor subject compared to a control, and (16) the determination kit according to any one of items (13) to (15) above, wherein the head-and-neck tumor is laryngeal cancer or squamous cell cancer.

The present invention yet further relates to (17) a method for screening therapeutic agents for head-and-neck tumor, comprising the steps of: (A) administering a test substance to a non-human animal suffering from head-and-neck tumor; (B) measuring the expression level of one or more microRNAs selected from the group of microRNAs consisting of miR-455-3p, miR-455-5p, miR-130b, miR-130b*, miR-801, miR-196a, miR-21, miR-31, miR-133b, miR-145 and miR-375 in a head-and-neck tumor tissue or blood of the non-human animal; and (C) comparing the above expression level to the expression level of the microRNA in the case of the test substance being unadministered as a control for evaluation, and (18) the screening method according to item (17) above, wherein the miR-455-3p, miR-455-5p, miR-130b, miR-130b*, miR-801, miR-196a, miR-21, miR-31, miR-133b, miR-145 and miR-375 are RNAs in which one or more nucleotides are deleted, substituted or added in the nucleotide sequences represented by SEQ ID NOs:1 to 11, respectively and whose expression increases or decreases in the head-and-neck tumor tissue or the blood of the head-and-neck tumor subject compared to a control.

Advantages of the Invention

The method for the determination of head-and-neck tumor and the method for using a microRNA as a biomarker for head-and-neck tumor according to the present invention enable the head-and-neck tumor to be rapidly and accurately determined. The kit for the determination of head-and-neck tumor and the method for using a microRNA for the determination of head-and-neck tumor according to the present invention also enable the rapid and accurate determination of the presence of the head-and-neck tumor. In addition, the method for screening therapeutic agents for head-and-neck tumor enables the therapeutic agents for head-and-neck tumor to be efficiently screened. Particularly, a microRNA (for example, miR-196a or the like) whose concentration in the blood of a subject also changes when a subject suffers from head-and-neck tumor is excellent especially in terms of speeding-up and simplifying the method for use as a biomarker for head-and-neck tumor, the method for the determination of head-and-neck tumor, and the like because a blood sample very easy to collect can be used. Further advances in research on the present microRNAs enable the prediction of onset, progress and prognosis and treatment of head-and-neck tumor, which can be expected to offer a breakthrough toward the solution of various current clinical problems with the head-and-neck tumor. The expression of a microRNA is known to be tissue-specific and also has a possibility of being useful for identification of the primary site of head-and-neck cancer of unknown primary origin. In the treatment of the tumor, if resistance to drug and radiation therapies can be diagnosed, it further has a possibility of being developed up to therapy for individual in which an effective therapy is selected for each individual patient. Accurate diagnosis and prediction of prognosis can be expected to reduce excessive tests and extra hospital visits, which is also expected to have a great medical economic effect.

BRIEF DESCRIPTION OF DRAWINGS

FIG. 1 A drawing summarizing samples for analyzing the expression profile of microRNAs.

FIG. 2 A drawing showing the results of quality checking of sample-derived total RNA using UV.

FIG. 6 A graph showing the relative expression level of miR-34 in normal tissues or tumor tissues of the larynx.

FIG. 7 A series of graphs showing the relative expression level of the let-7 family in normal tissues or tumor tissues of the larynx.

FIG. 15 A graph showing the relative expression level of miR-455-5p in human squamous cell cancer (SCC) cells and the like.

FIG. 16 A graph showing the relative expression level of miR-130b* in human squamous cell cancer (SCC) cells and the like.

FIG. 17 A graph showing the relative expression level of miR-196a in human squamous cell cancer (SCC) cells and the like.

FIG. 18 A graph showing the relative expression level of miR-133b in human squamous cell cancer (SCC) cells and the like.

FIG. 19 A graph showing the relative expression level of miR-375 in human squamous cell cancer (SCC) cells and the like.

FIG. 24a indicates a cancer area; FIG. 24b, a squamous epithelium part of a non-cancer area; FIG. 24c, a high magnified view of FIG. 24a; and FIG. 24d, a high magnified view of FIG. 24b.

BEST MODE OF CARRYING OUT THE INVENTION

Figure 3:
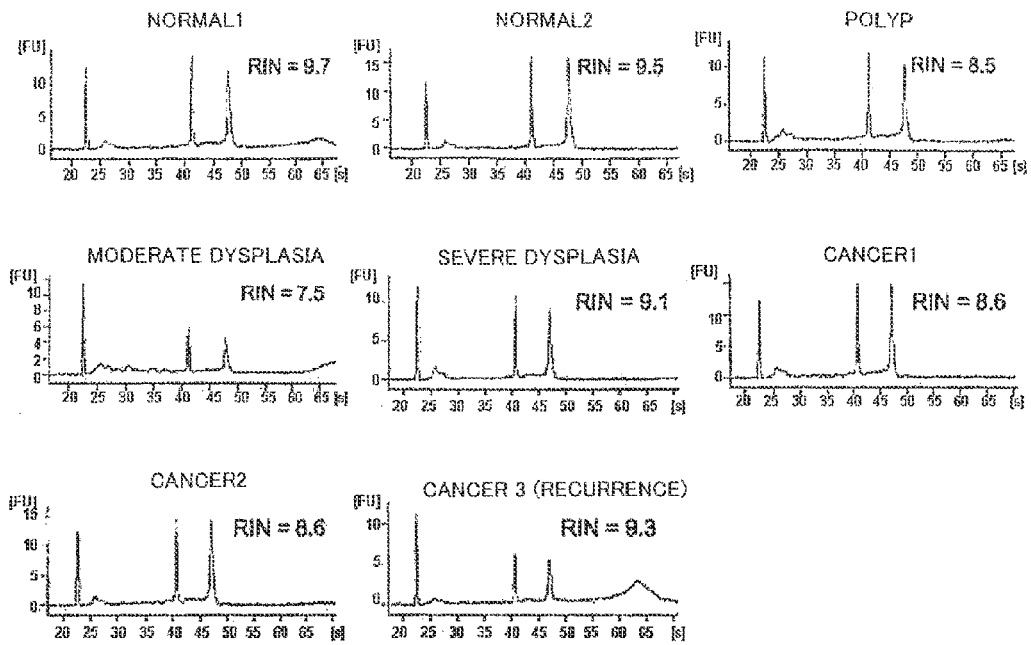
FIG. 3 A series of graphs showing the results of quality checking of sample-derived total RNA using Bio-Analyzer RNA6000.

The method for using a microRNA as a biomarker for head-and-neck tumor according to the present invention is not particularly limited provided that it is a method for using one or more microRNAs selected from the group of microRNAs consisting of miR-455-3p (microRNA-455-3p), miR-455-5p (microRNA-455-5p), miR-130b (microRNA-130b), miR-130b* (microRNA-130b*), miR-801 (microRNA-801), miR-196a (microRNA-196a), miR-21 (microRNA-21), miR-31 (microRNA-31), miR-133b (microRNA-133b), miR-145 (microRNA-145), and miR-375 (microRNA-375) (hereinafter also referred to as "the present microRNA") as a biomarker for head-and-neck tumor such as laryngeal cancer; specific examples thereof can include the method for the determination of head-and-neck tumor according to the present invention, the method for use for the determination of head-and-neck tumor according to the present invention, and the method for screening therapeutic agents for head-and-neck tumor according to the present invention.

Examples of the type of tumor in the above head-and-neck tumor can include head-and-neck cancer (incipient or recurrent), head-and-neck dysplasia, head-and-neck polyps, and squamous cell cancer; preferred examples thereof can include head-and-neck cancer (incipient or recurrent), head-and-neck dysplasia, and squamous cell cancer; more preferred examples thereof can include head-and-neck cancer (incipient or recurrent) and squamous cell cancer; and still more preferred examples thereof can include incipient head-and-neck cancer and incipient squamous cell cancer. Examples of the head and neck in the head-and-neck tumor herein can include head parts such as the lips, oral cavity, nasal and paranasal cavities, salivary gland, ear and temporal bones, and skull base and neck parts such as the pharynx, larynx, esophagus, and thyroid; preferred examples thereof can include neck parts; and among others, the larynx can be more preferably exemplified. Head-and-neck tumor in most cases is considered to have a tissue type derived from squamous epithelial cells as does the laryngeal cancer; thus, the present microRNA can also be used as a biomarker for head-and-neck tumor other than laryngeal cancer. In fact, as stated in Examples to be described later, the present microRNA can be used as a biomarker for squamous cell cancer as cancer of the oral cavity.

Preferred examples of living organisms from which the present microRNAs are derived can include mammals such as a human, a mouse, a rat, a hamster, a guinea pig, a monkey, a cow, a pig, a horse, a rabbit, sheep, a goat, a cat, and a dog; among others, a human and a mouse can be more preferably exemplified; and a human can be particularly preferably exemplified. The present microRNAs of human origin miR-455-3p, miR-455-5p, miR-130b, miR-130b*, miR-801, miR-196a, miR-21, miR-31, miR-133b, miR-145 and miR-375 have nucleotide sequences as represented by SEQ ID NOs:1 to 11, respectively. The sequence of microRNA is particularly high in conservativeness among mammals; the present microRNA even in mammals other than a human probably has an expression profile similar to that for a human. For example, the present microRNAs of mouse origin mmu miR-455-3p, mmu miR-130b*, mmu miR-801, mmu miR-196a, and mmu miR-31 have nucleotide sequences as represented by SEQ ID NOs:29 to 33, respectively.

For convenience the present microRNA includes RNA in which one or more nucleotides are deleted, substituted or added in the nucleotide sequences represented by SEQ ID NOs:1 to 11 and whose expression increases or decreases in a head-and-neck tumor tissue or blood of a head-and-neck tumor subject compared to a control. The above "at least one" is preferably 1 to 5, more preferably 1 to 3, particularly preferably 1 to 2, still more preferably 1. It can be easily confirmed, for example, by a microarray or quantitative PCR method to be described later whether the RNA consisting of a nucleotide sequence having deletion or the like increases or decreases in expression in the head-and-neck tumor tissue or blood of a head-and-neck tumor subject compared to a control. The present microRNAs from the above living organisms other than a human can be confirmed or identified based on the information deposited in databases such as GenBank. The above head-and-neck tumor subject means a subject suffering from head-and-neck tumor. Preferred examples of the "subject" herein can include mammals such as a human, a mouse, a rat, a hamster, a guinea pig, a monkey, a cow, a pig, a horse, a rabbit, sheep, a goat, a cat, and a dog; among others, a human and a mouse can be preferably exemplified; and a human can be particularly preferably exemplified.

The method for the determination of head-and-neck tumor according to the present invention is not particularly limited provided that it comprises the steps of: (A) extracting RNA from specimen tissue from the head and neck or blood of a subject; (B) measuring the amount of the present microRNAs in the extracted RNA; and (C) comparing the measured expression level with the expression level of the microRNAs in a normal tissue of the same type as that of the specimen tissue or in blood of a normal subject for evaluation; however, preferred examples thereof can include a method in which the tumor is determined as being head-and-neck tumor when the expression level of one or more microRNAs selected from the group of microRNAs consisting of miR-455-3p, miR-455-5p, miR-130b, miR-130b*, miR-801, miR-196a, miR-21, and miR-31 in the extracted RNA increases compared to a control and/or determined as being head-and-neck tumor when the expression level of one or more microRNAs selected from the group of microRNAs consisting of miR-133b, miR-145 and miR-375 in the extracted RNA decreases compared to a control. When the specimen tissue from the head and neck is used in the above step (A), a normal tissue of the same type as that of the specimen tissue is used as a control in the above step (C); and when the blood of the subject is used in the step (A), blood of a normal subject of the same species as that of the above subject is used as a control in the step (C). The expression level of a microRNA herein preferably uses the relative expression level corrected using a suitable internal standard gene to correct variations between samples in view of performing accurate determination. The internal standard gene is not particularly limited; examples thereof can include at least one gene selected from the group consisting of RNU48, RNU6b, snRNA (small nuclear RNA), and snoRNA (small nucleolar RNA); among others, RNU48 and/or RNU6b used as an internal standard gene in the expression analysis of microRNAs subsequent to Example 4 to be described later can be more preferably exemplified.

The method for extracting RNA in the above (A) step is not particularly limited provided that it is a method which involves extracting RNA comprising microRNAs from the specimen tissue from the head and neck or the blood of the subject; preferred examples thereof can include a method which involves extracting total RNA comprising microRNAs using mirVana miRNA Isolation Kit (from Applied Biosystems) according to the appended protocol. The specimen tissue from the head and neck is not particularly limited provided that it is a tissue from the head and neck derived from a living organism whose head-and-neck tumor is to be determined. Preferred examples of the living organism can include mammals such as a human, a mouse, a rat, a hamster, a guinea pig, a monkey, a cow, a pig, a horse, a rabbit, sheep, a goat, a cat, and a dog; among others, a human and a mouse can be preferably exemplified; and a human can be particularly preferably exemplified.

The method for measuring the expression level of the present microRNA in the above (B) step is not particularly limited provided that it is a method which can identify the amount of the present microRNA in RNA comprising microRNAs; preferred examples thereof can include: a method for using the kit for the determination of head-and-neck tumor such as laryngeal cancer according to the present invention, that is, the kit for the determination of head-and-neck tumor comprising a microarray including a polynucleotide consisting of a nucleic acid sequence complementary to the sequence of the present microRNA or a part thereof, capable of measuring the expression level of the present microRNA, the kit for the determination of head-and-neck tumor including a primer set capable of amplifying the sequence of the present microRNA, or the kit for the determination of head-and-neck tumor including a primer set capable of amplifying the sequence of the present microRNA and a fluorescent probe comprising a polynucleotide consisting of a nucleic acid sequence complementary to the sequence of the present microRNA or a part thereof; and the method for use for the determination of head-and-neck tumor such as laryngeal cancer according to the present invention, that is, the microarray method for using for the determination of head-and-neck tumor in which a microarray includes a polynucleotide consisting of a nucleic acid sequence complementary to the sequence of the present microRNA or a part thereof, capable of measuring the expression level of the present microRNA, the quantitative PCR method using a primer set capable of amplifying the sequence of the present microRNA for the determination of head-and-neck tumor, or the quantitative PCR method (fluorescent probe method) for the determination of head-and-neck tumor using a primer set capable of amplifying the sequence of the present microRNA and a fluorescent probe comprising a polynucleotide consisting of a nucleic acid sequence complementary to the sequence of the present microRNA or a part thereof.

The microarray method is not particularly limited provided that it can measure the expression level of the present microRNA; examples thereof can include a method which involves labeling the RNA extracted from a tissue with a label (preferably a fluorescent label), contacting the RNA with a microarray to which a probe consisting of a polynucleotide (preferably DNA) consisting of a nucleic acid sequence complementary to the microRNA to be identified or a part thereof is fixed for hybridization, washing the microarray, and measuring the expression level of the remaining microRNAs on the microarray.

The type of the nucleotide of the nucleic acid sequence is not particularly limited provided that it can specifically hybridize to the predetermined microRNA according to the present invention; however, preferred is DNA because of its high stability. The length of the part of the polynucleotide is not particularly limited provided that it specifically hybridizes to the predetermined microRNA according to the present invention; however, it is preferably 10 to 100 mers, more preferably 10 to 40 mers in view of securing the stability of hybridization. The polynucleotide or a part thereof can be obtained by chemical synthesis or the like using a method well known in the art.

The array to which the polynucleotide or a part thereof is fixed is not particularly limited; however, preferred examples thereof can include a glass substrate and a silicon substrate, and the glass substrate can be preferably exemplified. A method for fixing the polynucleotide or a part thereof to the array is not particularly limited; a well-known method may be used.

The kit for the determination of head-and-neck tumor comprising a microarray according to the present invention may further comprise any element, such as reagents used for a microarray method, including, for example, a reagent used for RNA-labeling reaction, a reagent used for hybridization, a reagent used for washing, and a reagent used for extracting RNA from a tissue in addition to the above-described microarray.

The microarray method can be specifically exemplified by a method which involves measuring the expression level of a microRNA on DNA Microarray Scanner (from Agilent Technologies) using Agilent Human miRNA V2 (from Agilent Technologies) according to the method described in Agilent Technologies' miRNA Microarray Protocol Version 1.5. The microarray to which the probe consisting of the polynucleotide or a part thereof is fixed can be prepared, for example, by synthesizing a polynucleotide based on the sequence information of the present microRNA to be measured and fixing it to a commercially available array.

The quantitative PCR method is not particularly limited provided that it is a method using a primer set capable of amplifying the sequence of the present microRNA and can measure the expression level of the present microRNA; conventional quantitative PCR methods such as an agarose electrophoresis method, an SYBR green method, and a fluorescent probe method may be used. However, the fluorescent probe method is most preferable in terms of the accuracy and reliability of quantitative determination.

The primer set for the quantitative PCR method means a combination of primers (polynucleotides) capable of amplifying the sequence of the present microRNA. The primers are not particularly limited provided that they can amplify the sequence of the present microRNA; examples thereof can include a primer set consisting of a primer consisting of the sequence of a 5' portion of the sequence of a predetermined microRNA of the present invention (forward primer) and a primer consisting of a sequence complementary to the sequence of a 3' portion of the microRNA (reverse primer). Here, the 5' means 5' to the sequence corresponding to the reverse primer when both primers were positionally compared in the sequence of a mature microRNA; the 3' means 3' to the sequence corresponding to the forward primer when both primers were positionally compared in the sequence of a mature microRNA.

Preferred examples of the 5' sequence of a microRNA can include a sequence 5' to the central nucleic acid of the microRNA sequence; preferred examples of the 3' sequence of the microRNA can include a sequence 3' to the central nucleic acid of the microRNA sequence. The length of each primer is not particularly limited provided that it enables the amplification of the microRNA; however, each primer is preferably a 7-to-10-mer polynucleotide. The type of the nucleotide of a polynucleotide as the primer is preferably DNA because of its high stability.

The fluorescent probe is not particularly limited provided that it comprises a polynucleotide consisting of a nucleic acid sequence complementary to the sequence of the present microRNA or a part thereof; preferred examples thereof can include a fluorescent probe capable of being used for the TaqMan (trade name) probe method (including one using the FRET principle) or the cycling probe method; the fluorescent probe capable of being used for the TaqMan (trade name) probe method can be particularly preferably exemplified. Examples of the fluorescent probe capable of being used for the TaqMan (trade name) probe method (excluding one using the FRET principle) or the cycling probe method can include a fluorescent probe in which a fluorochrome is labeled 5' thereof and a quencher is labeled on 3' thereof; particularly preferred examples of the probe can include probes such as Part Numbers 4378098 (for miR-455-5p), 4395225 (for miR-130b*), 4373104 (for miR-196a), 4373172 (for miR-133b), and 4373027 (for miR-375) from Applied Biosystems.

Examples of the fluorescent probe using the FRET principle can include a fluorescent probe in which a donor dye and an acceptor dye are labeled 5' and 3' thereof, respectively. The fluorochrome, quencher, donor dye, acceptor dye or the like used may be a commercially available one as needed.

The type of the nucleotide of the nucleic acid sequence in the fluorescent probe is not particularly limited provided that it can specifically hybridize to the present microRNA; however, it is preferably DNA because of its high stability. The length of the part of the polynucleotide is not particularly limited provided that it specifically hybridize to the predetermined microRNA according to the present invention; however, it is preferably 10 mers or more, more preferably 15 mers or more in view of securing the stability of hybridization and the part still more preferably has a number of nucleotides (1 to 3 mers) smaller than the number of nucleotides of a full-length microRNA of interest.

The primer set and the fluorescent probe can be obtained by chemical synthesis or the like using a method well known in the art. Preferred specific methods for quantitative PCR using the primer set and fluorescent probe can include a method which involves using TaqMan (trade name) microRNA Assays (from Applied Biosystems) according to the appended protocol. The kit for the determination of head-and-neck tumor including a primer set and a fluorescent probe may further comprise any element such as, for example, a reagent used for quantitative PCR reaction such as polymerase in addition to the above-described primer set.

The normal tissue of the same type as that of the specimen tissue (for example, a normal laryngeal tissue when the specimen tissue is a laryngeal tissue) as a control in the (C) step is preferably a tissue (normal region) of the same individual as that from which the specimen tissue is derived because it enables more accurate evaluation in the method involving comparison with the expression level of a microRNA in the normal tissue for evaluation. The normal tissue of the same type as that of the specimen tissue or the blood of the normal subject of the same species as that of the above subject as a control does not necessarily need to be collected in collecting the specimen tissue or the blood of the subject; the comparison may be performed with a calibration curve prepared in advance for the expression level of the present microRNA in the normal tissue or the blood of the normal subject for evaluation.

In this manner, based on the expression level of microRNAs contained in RNA in a specimen tissue or the blood of a subject, it can be determined whether the specimen tissue or the subject has head-and-neck tumor or not. As described above, an increase in the amount of miR-455-3p, miR-455-5p, miR-130b, miR-130b*, miR-801, miR-196a, miR-21, or miR-31 among the present microRNAs compared to a control can be determined as indicating head-and-neck tumor; a decrease in the amount of miR-133b, miR-145, or miR-375 there among compared to a control can be determined as indicating head-and-neck tumor.

Among the present microRNAs, miR-130b* and miR-196a are very little observed to be expressed in a normal tissue or the blood of a normal subject; thus, they are preferable in that they enable the more accurate determination of the presence of head-and-neck tumor. The measurement of the expression level of the present two or more microRNAs to compare with a control for evaluation is also preferable in that it enables the more accurate determination of the presence of head-and-neck tumor such as laryngeal cancer. Among the present microRNAs, microRNAs whose concentration in the blood of a subject changes when the subject suffers from head-and-neck tumor (e.g., miR-196a) are also very preferable in that they make the method of using them as a biomarker for head-and-neck tumor, the method for the determination of head-and-neck tumor, and the like particularly excellent in rapidity and simplicity since a blood sample, extremely easy to collect, can be utilized. Among the present microRNAs, miR-455-5p is highly expressed for severe dysplasia 2 times or more that for moderate dysplasia and miR-801 and miR-196a is lowly expressed for severe dysplasia not more than ½ times that for moderate dysplasia.

The degree of an increase in the expression level of the present microRNA when determined as indicating head-and-neck tumor can be, for example, preferably 50% or more, more preferably 75% or more, still more preferably 100% or more as a percentage relative to a control, and the degree of a decrease in the expression level of the present microRNA when determined as indicating head-and-neck tumor can be, for example, preferably 25% or more, more preferably 50% or more, still more preferably 75% or more as a percentage relative to a control.

In addition to the above steps (A) to (C), the method for the determination of head-and-neck tumor according to the present invention may further comprise the step of (D) measuring the expression level of one or more microRNAs selected from the group of microRNAs consisting of let-7 family, miR-17-92 cluster, miR-15, and miR-16 in the extracted RNA and comparing the expression level of the microRNA in the normal tissue of the same type as that of the specimen tissue or the blood of the normal subject of the same species as that of the above-described subject as a control for evaluation. Preferred examples of the member of the let-7 family can include let-7a, let-7b, let-7c, let-7d, let-7e, let-7f, let-7g, and let-7i. Preferred examples of the member of the miR-17-92 cluster can include miR-17, miR-18a, miR-19a, miR-19b, miR-20a, and miR-92a. Preferred examples of the miR-15 can include miR-15a and miR-15b. Particularly preferred examples of the microRNAs (let-7a, let-7b, let-7c, let-7d, let-7e, let-7f, let-7g, let-7i, miR-17, miR-18a, miR-19a, miR-19b, miR-20a, miR-92a, miR-15a, miR-15b, and miR-16) derived from a human can include RNAs consisting of nucleotide sequences represented by SEQ ID NOs:12 to 28, respectively.

Each of the microRNAs (let-7 family, miR-17-92 cluster, miR-15, and miR-16) in the step (D) shows abnormal expression in tumors other than head-and-neck tumor; thus, when the specimen tissue or the subject is determined to have head-and-neck tumor as a result of identification and evaluation in the step (B), the further observation of abnormal expression of such a microRNA in the step (D) can result in the determination that lesions of tumors other than head-and-neck tumor are present. In fact, the expression of the microRNA let-7 family or miR-15 and miR-16 is known to decrease in lung tumor tissue or chronic lymphatic leukemia or pancreas tumor tissue, respectively, and the expression of miR-17-92 cluster is known to increase in B cell lymphoma or lung tumor tissue.

Other preferred methods for the determination of head-and-neck tumor can include, for example, a method comprising the steps of: (A) measuring the expression level of one or more microRNAs selected from miR-455-3p, miR-455-5p, miR-130b, miR-130b*, miR-801, miR-196a, miR-21, miR-31, miR-133b, miR-145 and miR-375 in a specimen tissue of the head and neck; and (B) comparing the measured amount with the expression level of the microRNA in a normal tissue of the same type as that of the above specimen tissue as a control for evaluation. Such a determination method can be carried out by a well-known in situ hybridization method using a microRNA detection probe in which the above microRNA is labeled with a DIG label, a fluorescent label, or the like. The determination method can probably be applied to the decision of a resection stump during the surgery for a malignant tumor, the treatment strategy of deciding the range of lymph node dissection by determining the presence of metastasis in the so-called sentinel lymph node, and the like. In addition, the determination method has a possibility of providing a useful tool for the diagnosis in a paraffin-embedded biopsied tissue or a surgically excised specimen, diagnosis of the grades of atypism and malignancy of tumorous lesions typified by leukoplakia of the head and neck previously been forced to depend on the subjectivity of a pathologist, or the cytodiagnosis of lymph nodes suspected of tumor invasion or metastasis requiring accurate diagnosis from a few cells.

The method for screening therapeutic agents for head-and-neck tumor according to the present invention is not particularly limited provided that it comprises the steps of: (a) administering a test substance to a non-human animal suffering from head-and-neck tumor; (b) measuring the expression level of the present microRNA in a head-and-neck tumor tissue or blood of the non-human animal; and (c) comparing the measured amount with the expression level of the microRNA in the case of the test substance being unadministered as a control for evaluation. Preferred examples of the species of the non-human animal can include a mouse, a rat, a hamster, a guinea pig, a monkey, a cow, a pig, a horse, a rabbit, sheep, a goat, a cat, and a dog; among others, a mouse and a rat can be preferably exemplified. The non-human animal suffering from head-and-neck tumor may be a non-human animal having spontaneously suffered from head-and-neck tumor or a non-human animal in which head-and-neck tumor has been induced using a carcinogenic substance.

The method for measuring the expression level of the present microRNA in the step (b) may use the above-described method for measuring the expression level of the present microRNA. In the comparison/evaluation method in the step (c), the test substance can be determined as having a high possibility of being a therapeutic agent for head-and-neck tumor when miR-455-3p, miR-455-5p, miR-130b, miR-130b*, miR-801, miR-196a, miR-21, or miR-31 decreases compared to a control; the test substance can be determined as having a high possibility of being a therapeutic agent for head-and-neck tumor when miR-133b, miR-145, or miR-375 increases compared to a control. A microRNA is reported to have properties such as binding to mRNA to suppress the expression of gene; thus, such a test substance to shift the abnormal expression of the microRNA in the head-and-neck tumor tissue or blood toward normalization probably has a high possibility of being used as a therapeutic agent for head-and-neck tumor.

In place of the step (c), the step of (d) comparing the measured amount with the expression level of the microRNA in a normal tissue of the same type as that of the tumor tissue or blood of a normal subject of the same species as that of the above-described subject as a control for evaluation may be adopted. In the comparison/evaluation method of the step (d), the test substance can be determined as having a high possibility of being a therapeutic agent for head-and-neck tumor when the expression level of the present microRNA is not significantly different compared to a control.

Among the present microRNAs, miR-130b* and miR-196a are very little observed to be expressed in a normal tissue or blood of a normal subject; thus, they are preferable in that they enable the more accurate determination of a possibility that the substance is a therapeutic agent for head-and-neck tumor. The combined use of two or more of the above-described microRNAs as biomarkers for head-and-neck tumor is preferable in that it enables the more accurate determination of a possibility that the substance is a therapeutic agent for head-and-neck tumor. Among the present microRNAs, microRNAs whose concentration in the blood of a subject is changed when the subject suffers from head-and-neck tumor (e.g., miR-196a) are also very preferable in that they make the method of using them as a biomarker for head-and-neck tumor, the method for the determination of head-and-neck tumor, and the like particularly excellent in rapidity and simplicity since a blood sample, extremely easy to collect, can be utilized.

The present invention will be more specifically described below with reference to Examples. However, these Examples are not intended to limit the technical scope of the present invention.

Example 1

Collection of Sample Tissue—1

Under the approval of the ethics committees of Keio University School of Medicine and Sano Kosei General Hospital, patients visiting the otorhinolaryngology clinic of Keio University Hospital or Sano Kosei General Hospital were selected and used as persons to be asked for sample donation. Then, after obtaining informed consent from the persons, 8 sample tissues ("SAMPLE ID 1 to 8" in FIG. 1) were collected from 6 of the persons. In this respect, the sample ID 1 and 6 were those from the same patient, and the sample ID 2 and 7 were also those from the same patient. The tissue types of these 8 sample tissues (the article "TISSUES" in FIG. 1) consisted of two types: larynx and vocal cord; the tissue conditions (the article "SAMPLES" in FIG. 1) consisted of conditions: normal, polyp, moderate dysplasia, severe dysplasia and cancer conditions; and the types of the cancers consisted of two types: incipient cancer (incipient) for cancers 1 to 2 and recurrent cancer (recurrence; rec) for cancer 3.

A portion of each of the collected tissues was placed in a tube into which RNAlater (trade name) (from Applied Biosystems) was dispensed and subjected to frozen storage to stabilize RNA in each tissue. The condition (cancer, dysplasia, polyp or normal condition, or the like) of each sample tissue was subjected to definite diagnosis by performing the pathological examination of another portion of each of the collected tissues.

Example 2

Extraction of RNA from Sample Tissue and Qualitative Evaluation Thereof—1

RNA was extracted from each tissue frozen in Example 1 in order to use in a microarray to be described later. Specifically, total RNA comprising microRNAs was extracted from each of the above tissues using mirVanamiRNA Isolation Kit (from Applied Biosystems) according to the appended protocol.

Then, the extracted RNA was subjected to qualitative evaluation in order to make sure that sufficient accuracy would be obtained in the microarray to be described later. Specifically, the resultant RNA was adjusted to a concentration of about 30 ng/μL using distilled water, and OD260/280 (the numerical value obtained by dividing the measured value of OD260 by the measured value of OD280) and the like were measured using a spectrophotometer for calculation. The results are shown in FIG. 2. As shown in FIG. 2, each OD260/280 fell in the range of about 1.7 to 2.0, indicating that each RNA was little contaminated with protein and phenol and had good quality. RIN (RNA Integrity Number) of the extracted total RNA was measured using Bio-Analyzer RNA6000 (from Agilent Technologies) to examine the degree of RNA decomposition. The results are shown in FIG. 3. As shown in FIG. 3, RIN for each sample retained a sufficient high level, indicating that each RNA had good quality.

Example 3

Expression Analysis of microRNAs in Each Tissue—1

Using Agilent Human miRNA V2 (from Agilent Technologies), 723 human microRNAs were subjected to exhaustive analysis. The above-described Agilent Human miRNA V2 microarray comprises DNA sequences complementary to nucleotide sequences represented by SEQ ID NOs:1 to 11 as probes for miR-455-3p, miR-455-5p, miR-130b, miR-130b*, miR-801, miR-196a, miR-21, miR-31, miR-133b, miR-145 and miR-375, respectively. The method for analysis was according to the method described in Agilent Technologies' miRNA Microarray Protocol Version 1.5. Specifically, the analysis was performed by the following method. The amount of a reagent is described as an amount for one sample.

First, the total RNA obtained in Example 2 was diluted to about 25 ng/μL with DNase/RNase-free water, and the RNA concentration of the diluted solution was measured. Then, 0.7 μL of 10×CIP Buffer (from GE Healthcare) was mixed with 0.7 μL of 16 U/μL CIP (from GE Healthcare) to prepare 1.4 μL of a CIP master mix. The above diluted solution of RNA was dispensed in such an amount that the total RNA amount is 100 ng, into a 1.5-mL tube, to which 1.4 μL of the above CIP master mix was added, followed by further adjusting the resultant solution to 7 μL with DNase/RNase-free water. Thereafter, the solution was incubated at 37° C. for 30 minutes to perform the dephosphorylation of the total RNA.

DMSO (from Sigma) (5 μL) was added to the sample solution subjected to dephosphorylation, which was then mixed and incubated at 100° C. for about 5 minutes to perform the thermal denaturation of the total RNA. Immediately thereafter, it was cooled with ice water for 2 minutes.

Then, ligation was carried out. Specifically, 2 μL of 10×T4RNA Ligase Buffer (from GE Healthcare), 2 μL of 0.1% BSA (from GE Healthcare), 1 μL of T4 RNA Ligase (from GE Healthcare) adjusted to 15 U/μL, and 3 μL of Cyanine 3-Cytidine (from Agilent Technologies) were mixed in another 1.5-mL tube to prepare a ligation master mix. The ligation master mix (8 μL) was added to the above sample subjected to thermal denaturation and then cooled, which was then incubated at 16° C. for 2 minutes.

Subsequently, the sample was purified. Specifically, using MicroBioSpin6 (from BioRad) according to the appended protocol, a sample RNA fluorescently labeled with Cyanine 3-Cytidine was purified from the above sample.

The Agilent Human miRNA V2 (from Agilent Technologies) oligo DNA microarray was used to perform the microRNA profile analysis of the above sample RNA. According to Agilent Technologies' protocol, the RNA sample was subjected to hybridization reaction at 55° C. for 20 hours or more. Next, the microarray after hybridization was washed with washing buffer 1 at room temperature for 5 minutes and with washing buffer 2 at 37° C. for 5 minutes according to the Agilent Technologies' protocol. The microarray was pulled up from the washing buffer 2 and scanned using DNA Microarray Scanner (from Agilent Technologies).

Figure 4:
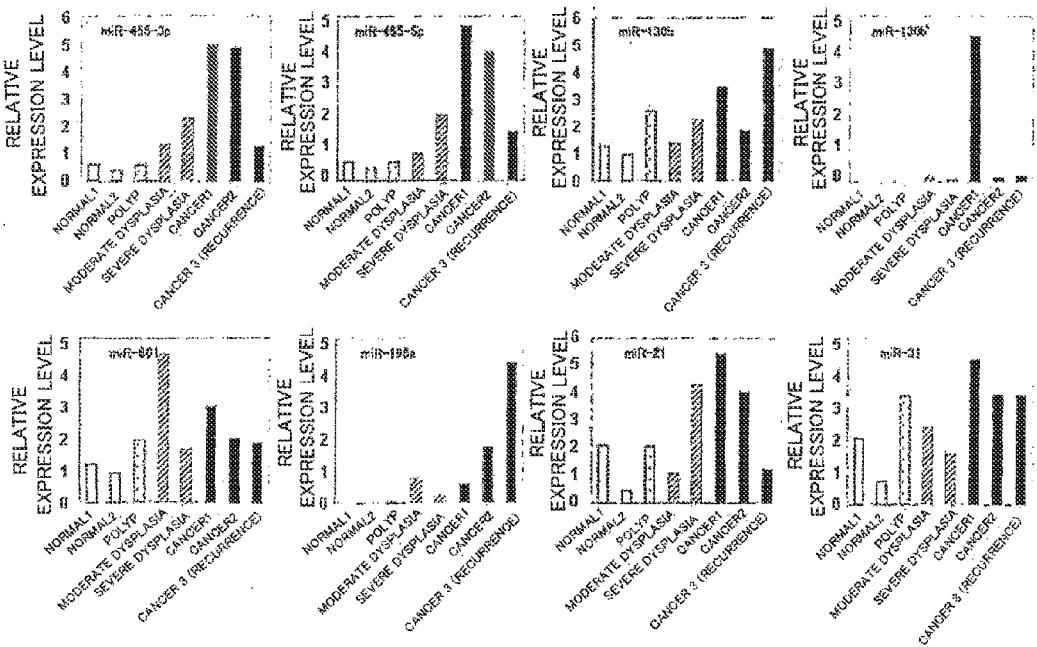
FIG. 4 A series of graphs showing the relative expression level of microRNAs (miR-455-3p, miR-455-5p, miR-130b, miR-130b*, miR-801, miR-196a, miR-21, and miR-31) whose expression increases in laryngeal tumor tissues such as laryngeal cancer tissue in each sample.
Figure 5:
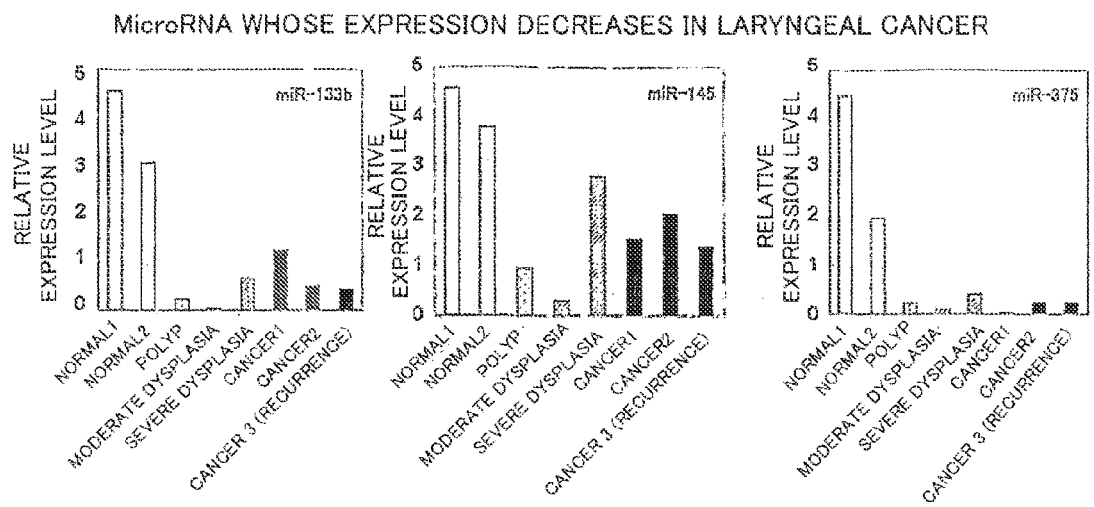
FIG. 5 A series of graphs showing the relative expression level of microRNAs (miR-133b, miR-145 and miR-375) whose expression decreases in laryngeal tumor tissues such as laryngeal cancer tissue in each sample.

Of 723 microRNAs, a plurality of microRNAs were found which show large differences in the expression level (signal intensity) between the normal laryngeal tissue (NORMAL 1 and 2) and the laryngeal tumor tissue (SAMPLE ID 4 to 8) (particularly, laryngeal cancer tissue: CANCER 1 to 3). The signal intensities of these microRNAs in each sample are shown in FIGS. 4 and 5. FIG. 4 shows microRNAs whose expression increases in laryngeal tumor tissues such as laryngeal cancer (miR-455-3p, miR-455-5p, miR-130b, miR-130b*, miR-801, miR-196a, miR-21, and miR-31); FIG. 5 shows microRNAs whose expression decreases in laryngeal tumor tissues such as laryngeal cancer (miR-133b, miR-145 and miR-375). These microRNAs can be used as markers for laryngeal tumor tissues such as laryngeal cancer because the microRNAs were expressed in the laryngeal tumor tissues such as laryngeal cancer in a manner different from the expression of those in the normal tissues (abnormal expression).

Figure 8:
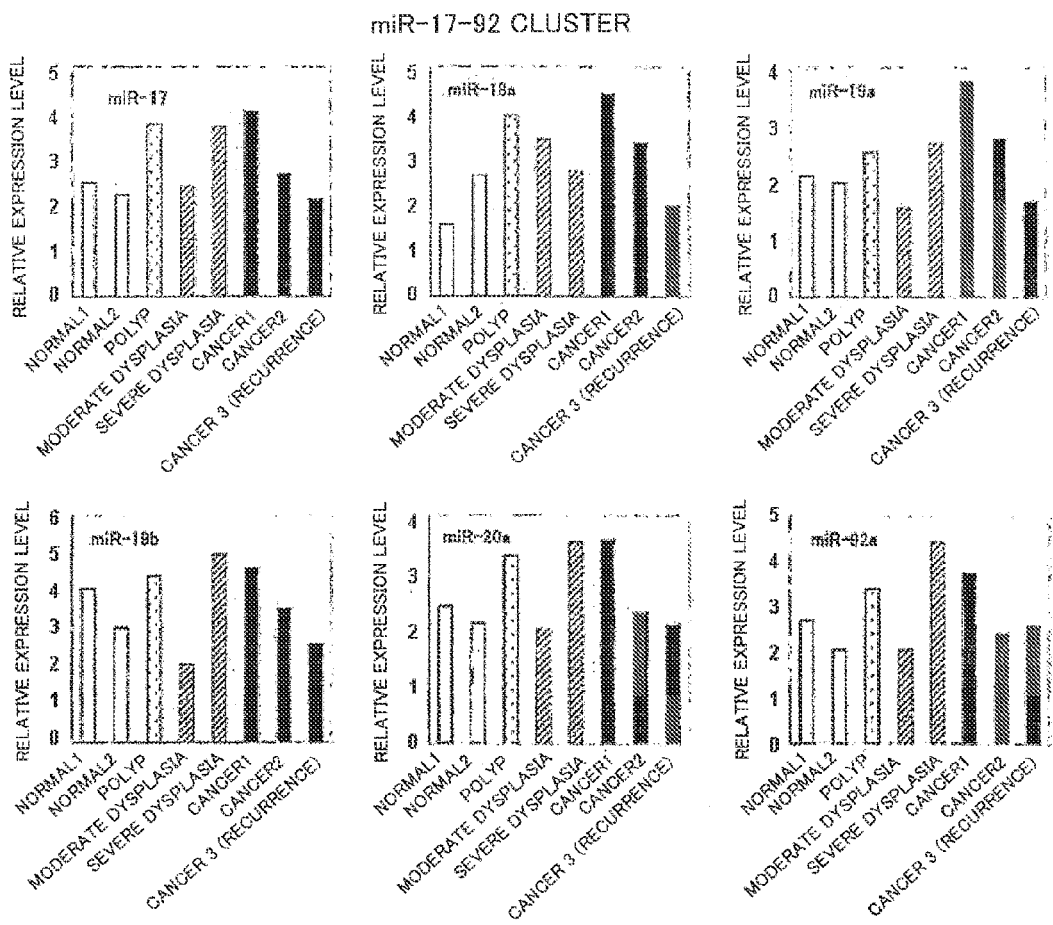
FIG. 8 A series of graphs showing the relative expression level of the miR-17-92 cluster in normal tissues or tumor tissues of the larynx.
Figure 9:
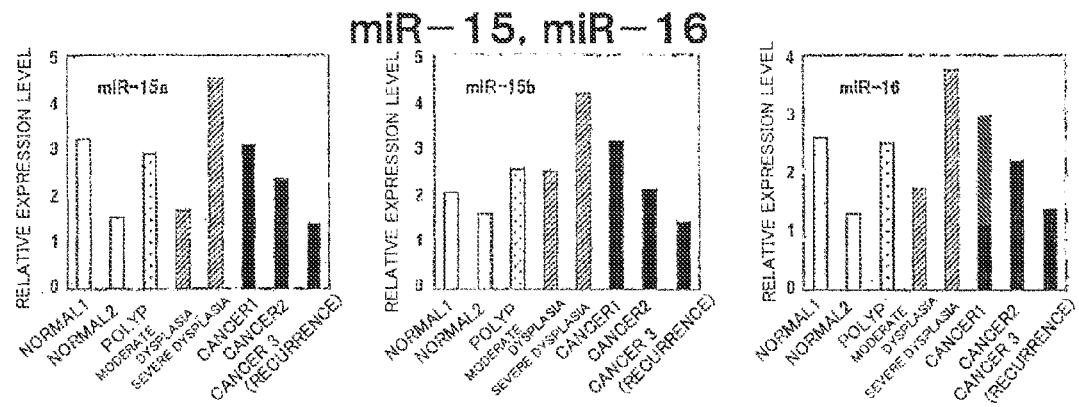
FIG. 9 A set of graphs showing the relative expression level of miR-15 and miR-16 in normal tissues or tumor tissues of the larynx.

The expression of miR-34, which is thought to take part in the suppression of canceration, was checked for each sample; however, abnormal expression was not particularly found for laryngeal tumor (FIG. 6). The expression of the members of the let-7 family (let-7a, let-7b, let-7c, let-7d, let-7e, let-7f, let-7g, and let-7i), miR-17-92 cluster (miR-17, miR-18a, miR-19a, miR-19b, miR-20a, and miR-92a), miR-15 (miR-15a and miR-15b), and miR-16, which were known to be abnormally expressed in other cancers, was checked for each sample; however, abnormal expression was not particularly found for laryngeal tumor (FIGS. 7, 8, and 9).

Example 4

Collection of Sample Tissue—2

Under the approval of the ethics committees of Keio University School of Medicine and Sano Kosei General Hospital, patients visiting the otorhinolaryngology clinic of Keio University Hospital or Sano Kosei General Hospital were selected and used as persons to be asked for sample donation. Then, after obtaining informed consent from the persons, laryngeal tumor tissues (laryngeal cancer) and tissues adjacent to thereto and pathologically recognized as non-cancer parts (non-cancer parts) were collected from 6 of the persons (patients 1 to 6) to provide 12 sample tissues.

A portion of each of the collected tissues was placed in a tube into which RNAlater (trade name) (from Applied Biosystems) was dispensed and subjected to frozen storage to stabilize RNA in each tissue. The condition (cancer or normal condition, or the like) of each sample tissue was subjected to definite diagnosis by performing the pathological examination of another portion of each of the collected tissues.

Example 5

Extraction of RNA from Sample Tissue and Qualitative Evaluation Thereof—2

RNA was extracted from each tissue frozen in Example 4 in order to use for real-time PCR to be described later. Specifically, total RNA comprising microRNAs was extracted from each of the above tissues using mirVana miRNA Isolation Kit (from Applied Biosystems) according to the appended protocol.

Then, the extracted RNA was subjected to qualitative evaluation in order to make sure that sufficient accuracy would be obtained in a real-time PCR to be described later. From the values of OD260/280 and RIN (RNA Integrity Number) for the extracted RNA, it was confirmed that these RNA had sufficiently good quality.

Example 6

Expression Analysis of microRNAs in Each Tissue—2

Figure 10:
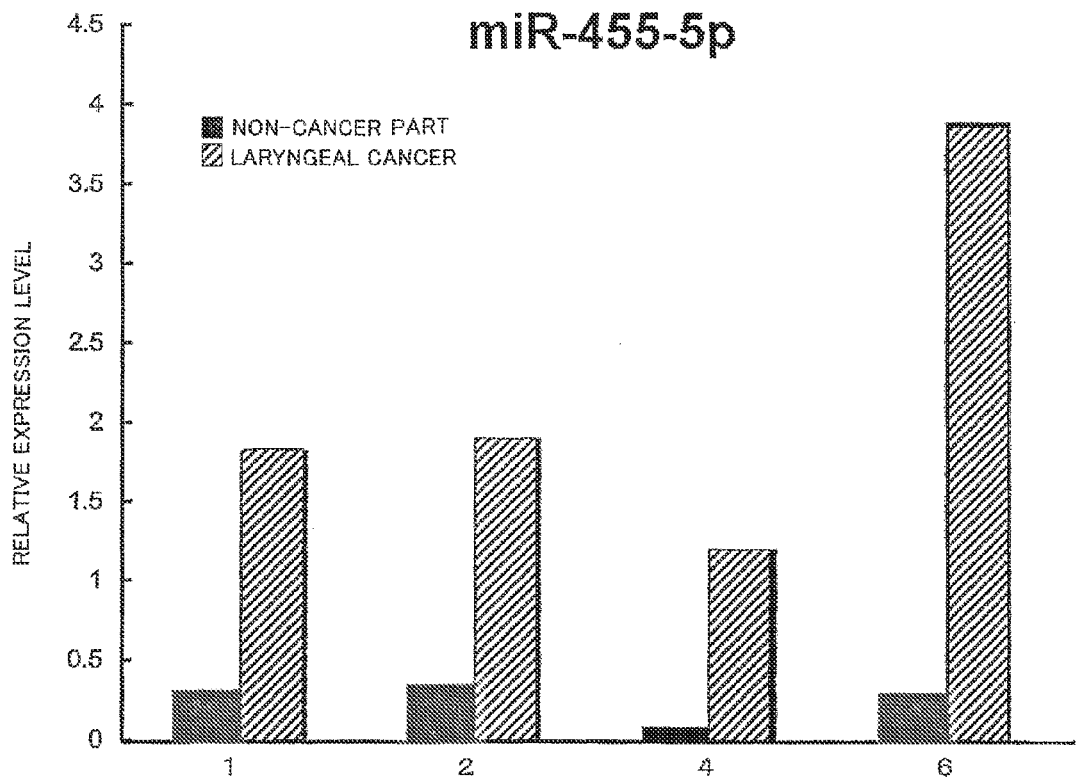
FIG. 10 A graph showing the relative expression level of miR-455-5p in laryngeal cancer tissues and the like. A left bar graph for each patient shows the result in a non-cancer area and a right bar graph shows the result in laryngeal cancer.
Figure 11:
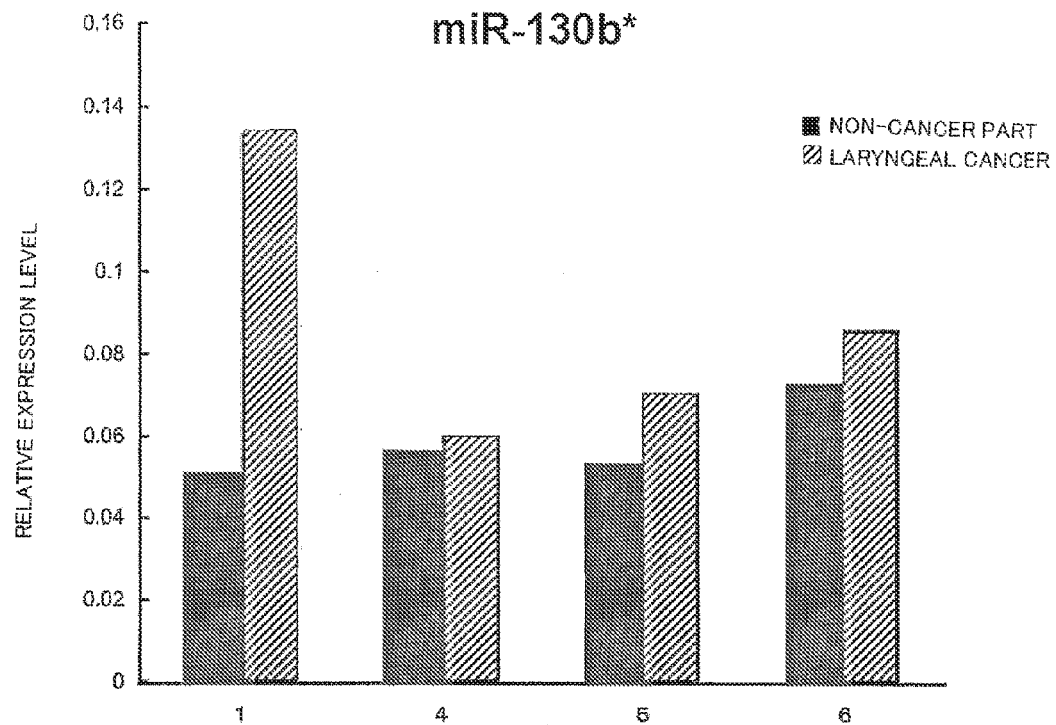
FIG. 11 A graph showing the relative expression level of miR-130b* in laryngeal cancer tissues and the like. A left bar graph for each patient shows the result in a non-cancer area and a right bar graph shows the result in laryngeal cancer.
Figure 12:
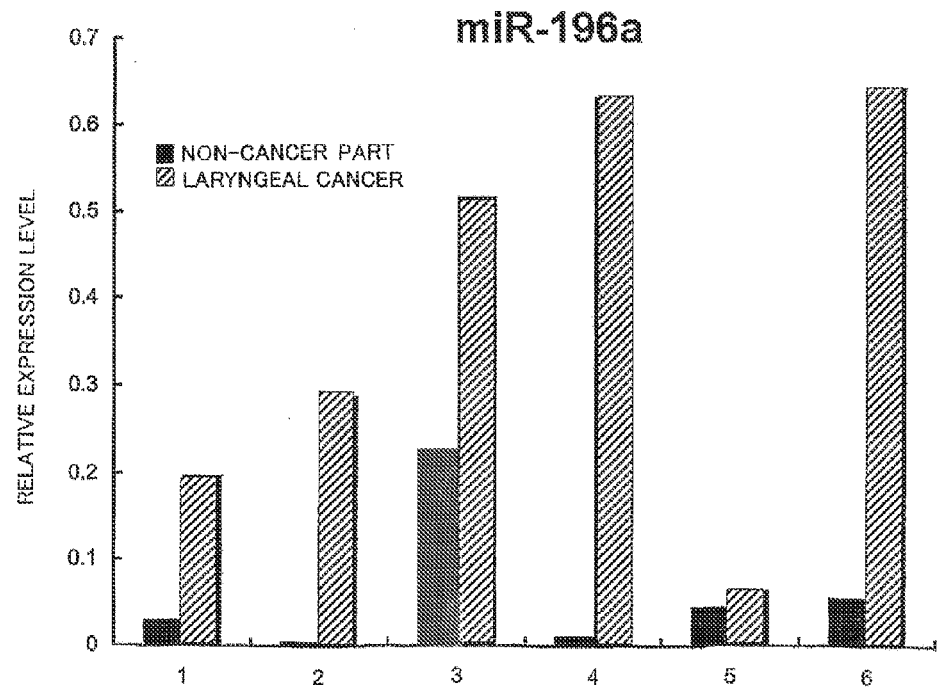
FIG. 12 A graph showing the relative expression level of miR-196a in laryngeal cancer tissues and the like. A left bar graph for each patient shows the result in a non-cancer area and a right bar graph shows the result in laryngeal cancer.
Figure 13:
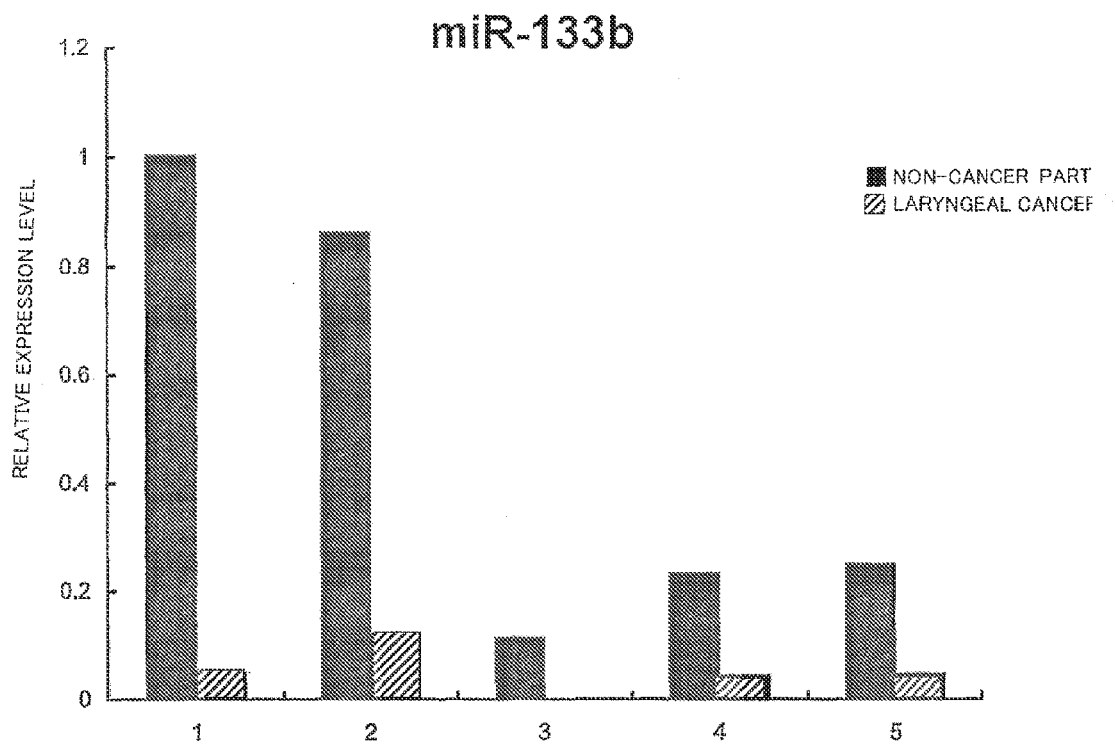
FIG. 13 A graph showing the relative expression level of miR-133b in laryngeal cancer tissues and the like. A left bar graph for each patient shows the result in a non-cancer area and a right bar graph shows the result in laryngeal cancer.
Figure 14:
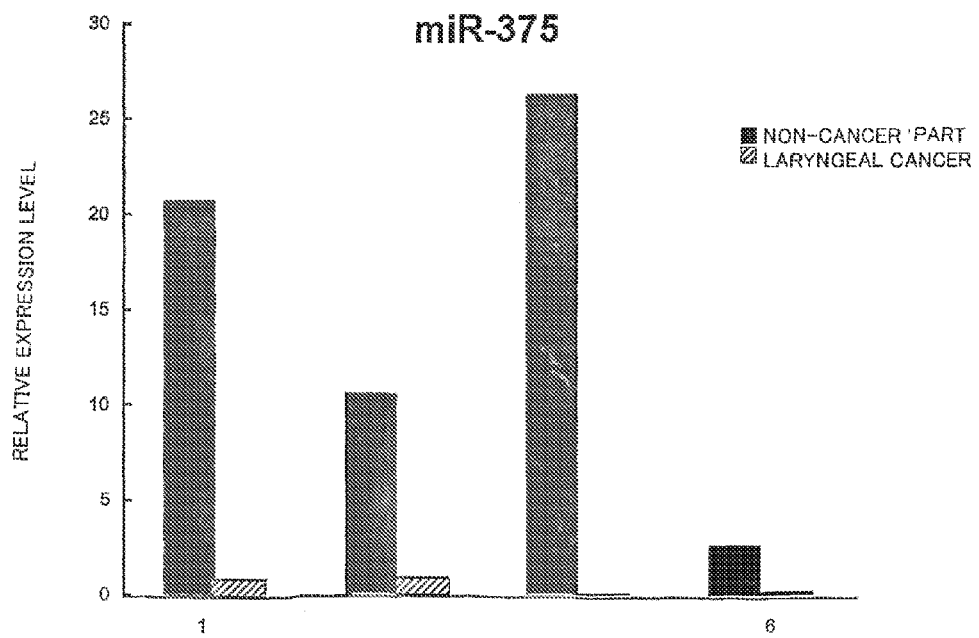
FIG. 14 A graph showing the relative expression level of miR-375 in laryngeal cancer tissues and the like. A left bar graph for each patient shows the result in a non-cancer area and a right bar graph shows the result in laryngeal cancer.

Using the RNA extracted in the above Example 5 and TaqMan (trade name) MicroRNA Assay (from Applied Biosystems), the expression level of miR-455-5p, miR-196a, miR-130b*, miR-133b, and miR-375 was quantitatively determined by the real-time PCR method. The method for quantitative determination was according to the method described in the appended protocol. The results of quantitative determination of miR-455-5p for the samples derived from patients 1 to 2, 4 and 6 are shown in FIG. 10; the results of quantitative determination of miR-130b* for the samples derived from patients 1 and 4 to 6, in FIG. 11; the results of quantitative determination of miR-196a for the samples derived from patients 1 to 6, in FIG. 12; the results of quantitative determination of miR-133b for the samples derived from patients 1 to 5, in FIG. 13; and the results of quantitative determination of miR-375 for the samples derived from patients 1 to 2, 4 and 6, in FIG. 14. As shown in FIGS. 10 to 12, the expression of miR-455-5p, miR-133b*, and miR-196a could be confirmed to increase in the laryngeal cancer tissues compared to the non-cancer parts. As shown in FIGS. 13 to 14, the expression of miR-133b and miR-375 could be confirmed to decrease in the laryngeal cancer tissues compared to the non-cancer parts.

Example 7

Extraction of RNA from Human Squamous Cell Cancer Cells and Qualitative Evaluation Thereof In order to demonstrate that the microRNAs according to the present invention can also be used as biomarkers for head-and-neck tumors other than laryngeal cancer, total RNA was extracted from cells of human squamous cell cancer cell lines (HSC2, HSC3, HSC4, SAS, and CA922). Specifically, using mirVana miRNA Isolation Kit (from Applied Biosystems) according to the appended protocol, total RNA comprising microRNAs was extracted from the above cells.

Then, the extracted RNA was subjected to qualitative evaluation in order to make sure that sufficient accuracy would be obtained in a real-time PCR to be described later. From the values of OD260/280 and RIN (RNA Integrity Number) for the extracted RNA, it was confirmed that these RNA had sufficiently good quality.

Example 8

Expression Analysis of microRNAs in Human Squamous Cell Cancer Cells

Figure 15:
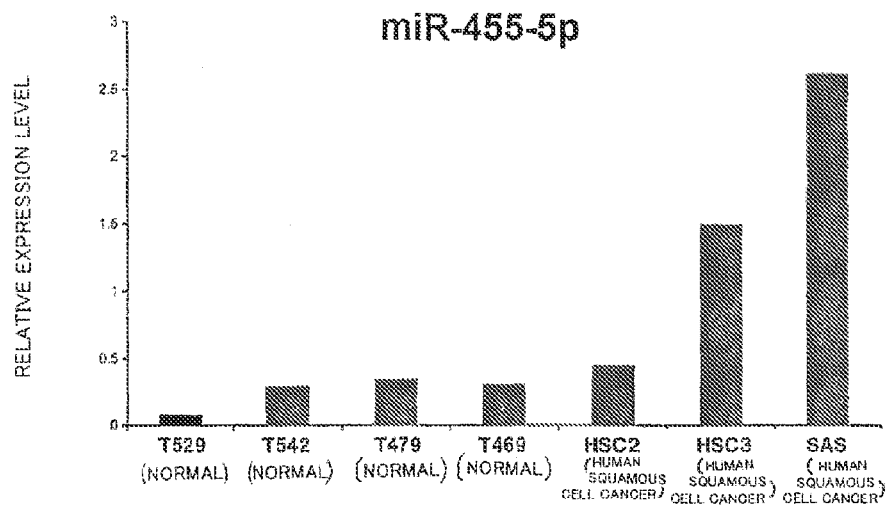
Figure 16:
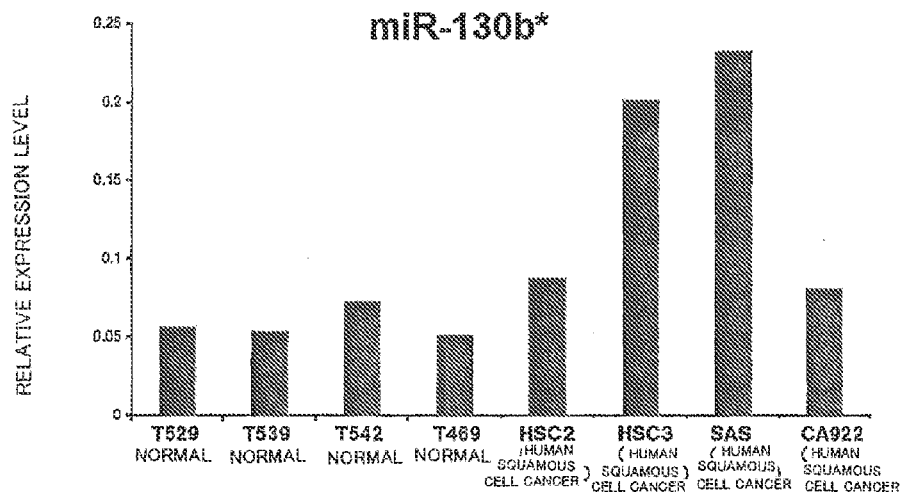
Figure 17:
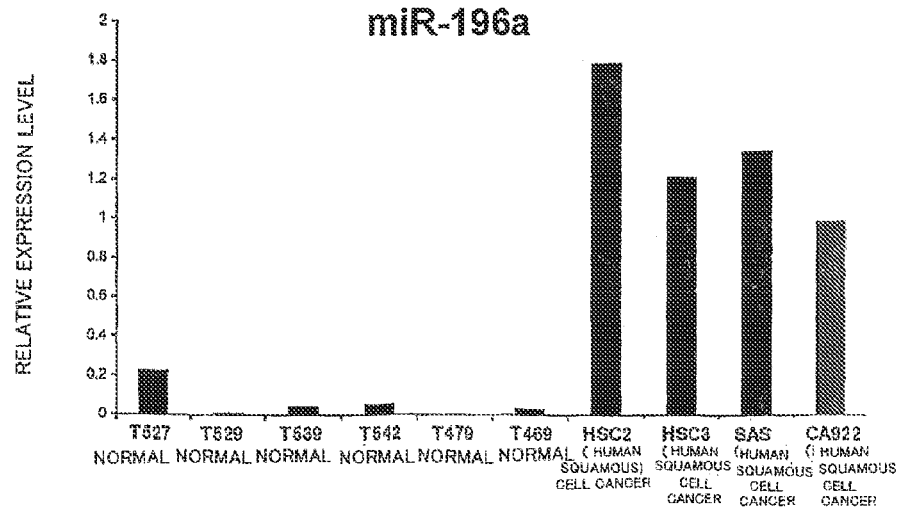
Figure 18:
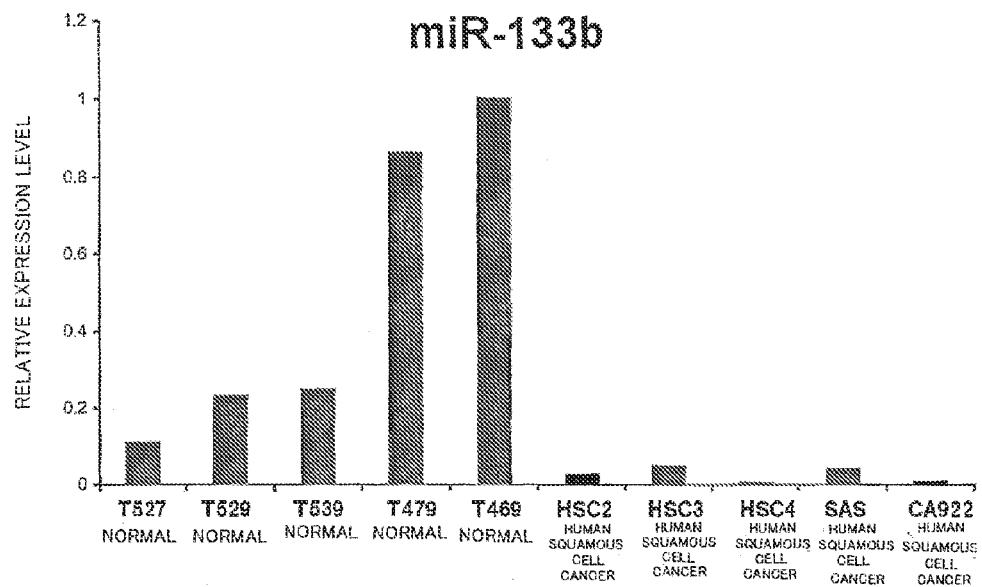
Figure 19:
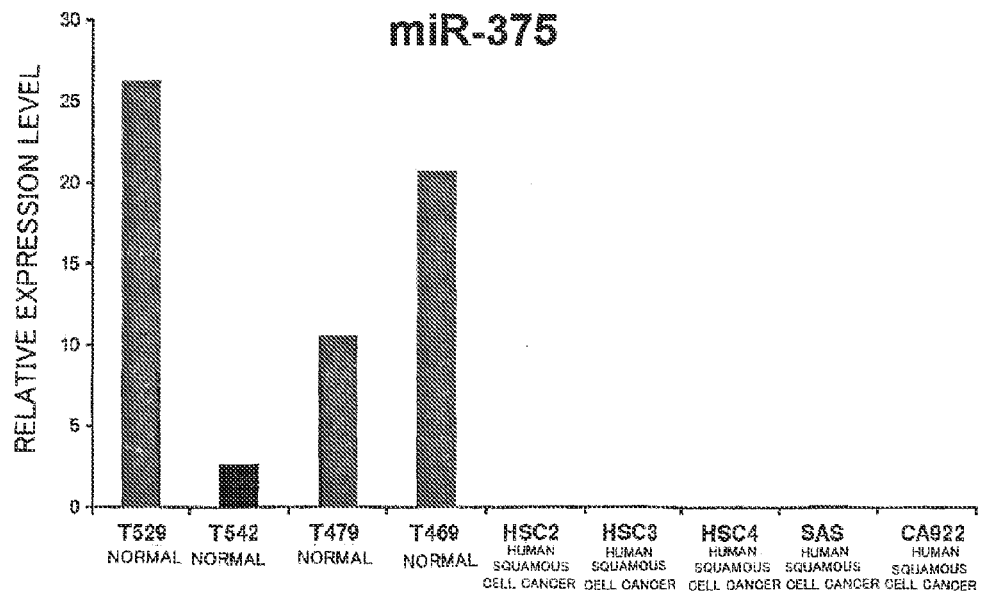

Using the RNA extracted in the above Example 7 and TaqMan (trade name) MicroRNA Assay (from Applied Biosystems), the expression level of miR-455-5p, miR-130b*, miR-196a, miR-133b, and miR-375 was quantitatively determined by the real-time PCR method. The method for quantitative determination was according to the method described in the appended protocol. As TaqMan probes for the real-time PCR, probes: Part Number 4378098, 4395225, 4373104, 4373172, and 4373027 were used for miR-455-5p, miR-130b*, miR-196a, miR-133b, and miR-375, respectively. As a control, microRNAs in the total RNA extracted from the normal tissues (NORMAL) in the above Example were also quantitatively determined. The results of quantitatively determining the expression level of miR-455-5p, miR-130b*, miR-196a, miR-133b, and miR-375 for the squamous cell cancer (SCC) cell-derived samples and the normal tissue cell-derived samples are shown in FIGS. 15 to 19. As shown in FIGS. 15 to 17, the expression of miR-455-5p, miR-133b*, and miR-196a could be confirmed to increase in the squamous cell cancer (SCC) cells compared to that in the non-cancer areas (NORMAL). As shown in FIGS. 18 to 19, the expression of miR-133b and miR-375 could be confirmed to decrease in the squamous cell cancer (SCC) cells compared to that in the non-cancer areas (NORMAL).

Example 9

Expression Analysis of microRNAs in Each Tissue—3

Figure 20:
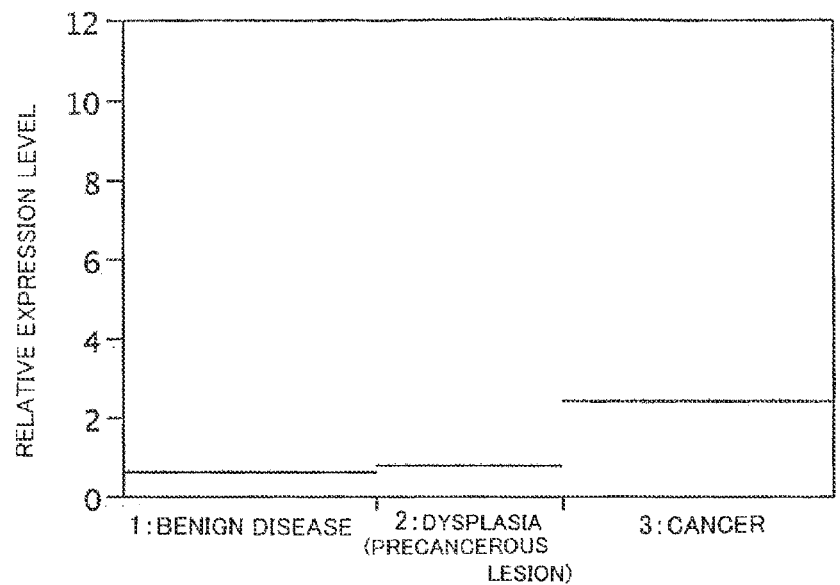
FIG. 20 A graph showing the average relative expression level of miR-455-5p in benign disease, precancerous lesion and cancer.
Figure 21:
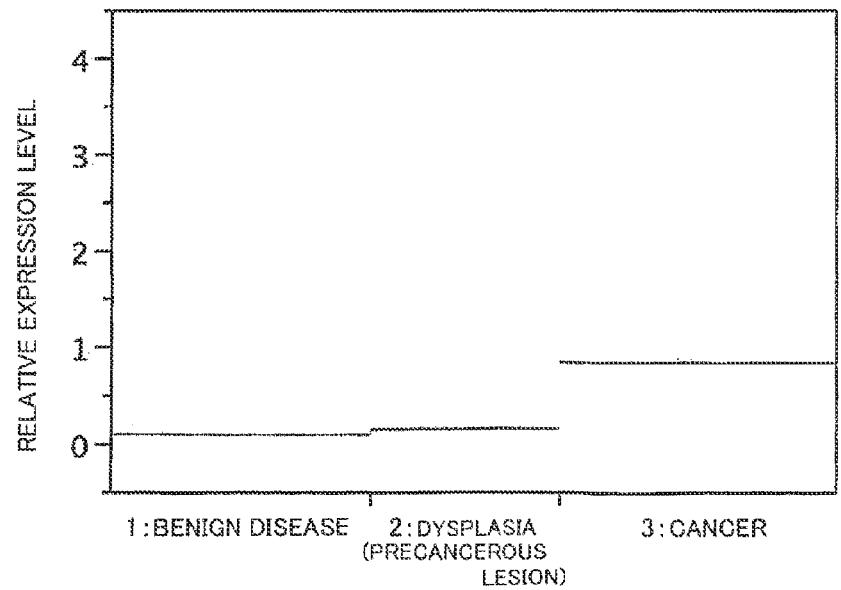
FIG. 21 A graph showing the average relative expression level of miR-196a in benign disease, precancerous lesion and cancer.
Figure 22:
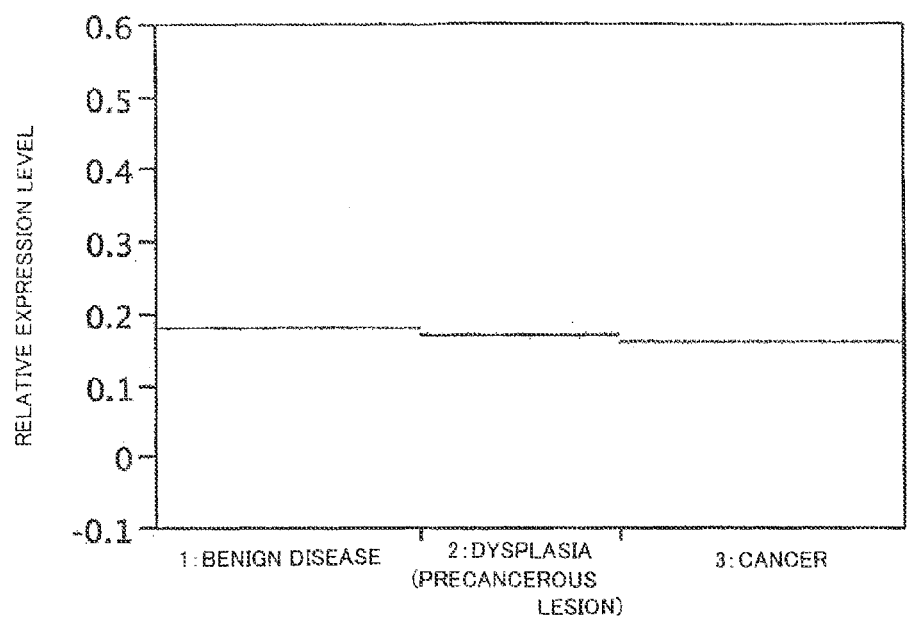
FIG. 22 A graph showing the average relative expression level of miR-133b in benign disease, precancerous lesion and cancer.

According to the same method as the method for expression analysis of microRNAs in the above-described Examples 4 to 6, the expression analysis of miR-455-5p, miR-196a, and miR-133b was carried out in tissues having benign disease (BENIGN) (16 samples), precancerous lesions (DYSPLASIA) (10 samples) and cancer (CANCER) (16 samples) in the larynx. The results of each samples averaged for each tissue are shown in FIGS. 20, 21 and 22 for the microRNAs (miR-455-5p, miR-196a, and miR-133b, respectively). As shown in FIGS. 20 and 21, the expression level of miR-455-5p and miR-196a was observed to tend to gradually increase as the tissue transfers from the benign disease to precancerous lesions to cancer. As shown in FIG. 22, the expression level of miR-133b was observed to tend to gradually decrease as the tissue transfers from the benign disease to precancerous lesions to cancer. As a result of the same expression analysis, miR-130b* showed the same tendency as that for miR-455-5p and miR-196a, and miR-375 showed the same tendency as that for miR-133b. Thus these microRNAs (particularly, miR-455-5p, miR-196a, and miR-133b) were observed to tend to change in the expression level with the degree of malignancy of cancer; thus, they proved to be capable of being particularly suitably used for the determination of head-and-neck tumor.

Example 10

Measurement of Concentration of microRNAs in Blood Before and After Removal of Cancer in Laryngeal Cancer Patients To examine whether or not, among the present microRNAs usable as biomarkers for head-and-neck tumor, there are any microRNAs enabling the determination of the presence of head and neck tissue tumor by using a blood sample of a subject instead of using a head-and-neck tissue sample, the following measure experiment was carried out.

Under the approval of the ethics committee of Keio University School of Medicine, a patient visiting Keio University Hospital was selected and used as a person to be asked for sample donation. Then, after obtaining informed consent from the person, a blood sample was collected from the patient (subject). This patient was a 61-year old man suffering from progressive laryngeal cancer and had undergone total extirpation of the larynx for cervical lymph node metastasis. The collection of a blood sample from the patient was performed immediately before the total extirpation of the larynx and after a lapse of 30 days from the total extirpation of the larynx.

RNA was extracted from the collected blood sample using mirVana PARIS (from Ambion) according to the appended protocol. Specifically, the extraction was carried out by the following method. First, the serum obtained from the blood sample was suspended and 300 µL thereof was dispensed into a new tube, to which 300 µL of 2× denaturing solution was then added, followed by allowing to stand on ice for 5 minutes. Then, 600 µL of acid-phenol: chloroform was added thereto and vortexed, followed by centrifugation at 10,000 g and room temperature for 5 minutes to recover the separated aqueous phase (650 µL). To the recovered solution was added 812.5 µL of 100% ethanol at room temperature, and 700 µL first separated from the resultant solution was dispensed onto a filter cartridge, and centrifuged at 10,000 g and room temperature for 30 seconds to pass the solution across the filter cartridge. The passed solution was discarded. Again, 700 µL was separated from the rest of the solution from which 700 µL had been separated earlier, dispensed onto the filter cartridge, and centrifuged at 10,000 g and room temperature for 30 seconds to pass the solution across the filter cartridge. The passed solution was discarded. Onto the filter cartridge was added 700 µL of wash solution 1, which was then centrifuged at 10,000 g and room temperature for 15 seconds to pass the wash solution 1 across the filter cartridge. The passed solution was discarded. Then, onto the filter cartridge was added 500 µL of wash solution 2/3, which was then centrifuged at 10,000 g and room temperature for 15 seconds to pass the wash solution 2/3 across the filter cartridge. The passed solution was discarded. Again, onto the filter cartridge was added 500 µL of wash solution 2/3, which was then centrifuged at 10,000 g and room temperature for 15 seconds to pass the wash solution 2/3 across the filter cartridge. The passed solution was discarded. Thereafter, after centrifugation at 10,000 g for one minute, the column was replaced with a new tube. Onto the filter cartridge was added 50 µL of deionized distilled water at 95° C. to elute the RNA adsorbed to the filter cartridge, followed by centrifuging the eluate at 10,000 g and room temperature for 30 seconds to provide an RNA extracted solution. The resultant RNA extracted solution was stored at −80° C.

Figure 23:
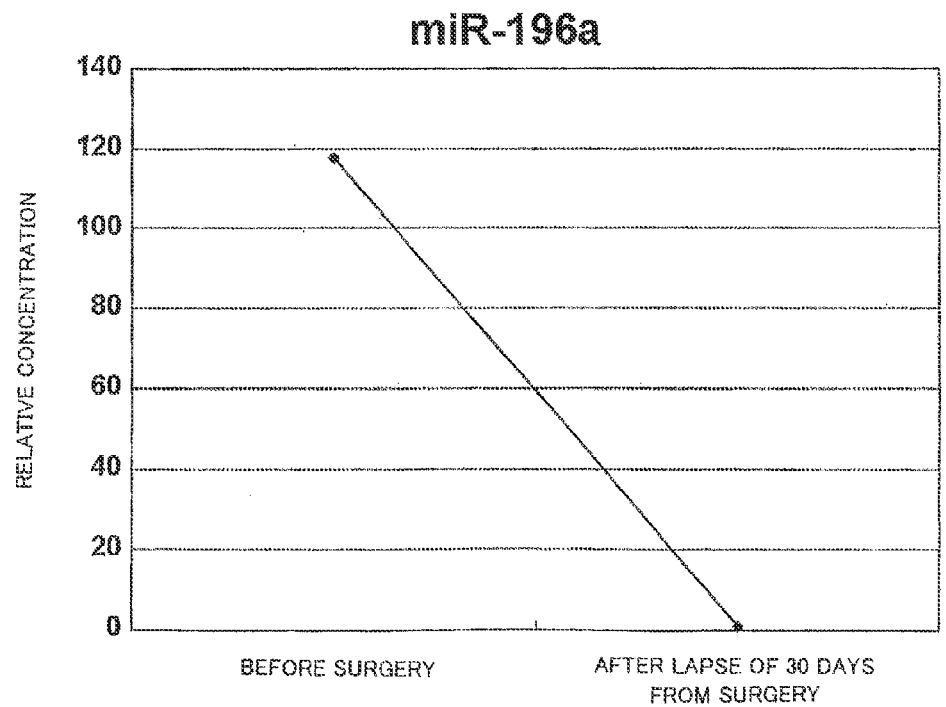
FIG. 23 A graph showing the relative concentration of miR-196a in blood before, and after a lapse of 30 days from, total extirpation of the larynx in a progressive laryngeal cancer patient. The numerical value of the relative concentration in the figure is expressed by setting the concentration of miR-196a in blood after a lapse of 30 days from total extirpation of the larynx to 1.

RNA extracted solutions were obtained from blood samples before and after total extirpation of the larynx by the above method for extracting RNA. The microRNA concentration in these two RNA extracted solutions was measured for miR-196a and miR-455-5p. The microRNA concentration was measured by counting the number of cycles of PCR reaction required until the microRNA to be measured exceeded a predetermined concentration, by a real-time PCR method using TaqMan (trade name) MicroRNA Assays (from Applied Biosystems). As a result, the concentration of miR-455-5p was little different between in the blood samples before total extirpation of the larynx and after a lapse of 30 days from total extirpation of the larynx, but as shown in FIG. 23, the concentration of miR-196a in the blood sample after a lapse of 30 days from total extirpation of the larynx (30 day post-0p) was found to be reduced to about 1/120 the concentration thereof in the blood sample before total extirpation of the larynx (pre-0p). This result shows that the concentration of some of the present microRNAs is changed not only in head-and-neck tumor tissue but also in a blood sample and these microRNAs can be used as biomarkers for head-and-neck tumor by using the change in the concentration thereof as an index.

Example 11

In Situ Hybridization in Isolated Larynx of Laryngeal Cancer Patient

To confirm whether a microRNA could be detected in a tissue, a specimen in which an isolated larynx of a patient with advanced laryngeal cancer was formalin-fixed and paraffin-embedded was used to perform in situ hybridization to hsa-miR-196a. A positively stained portion was color-developed (blue) with BICP/NBT, and nuclear staining (pink) was carried out with Kernechtrot. As a result, as shown in FIG. 24, while miR-196a was clearly detected in a cancer area (FIG. 24a and its high magnified view, FIG. 24c), almost no expression thereof was observed in the squamous epithelium part of a non-cancer area (FIG. 24b and its high magnified view, FIG. 24d).

In addition, even for laryngeal cancer specimens from non-Japanese subjects, the strong expression of hsa-miR-196a was also observed in laryngeal cancer tissues. The staining results of representative two specimens are shown in FIG. 25.

Figure 24:
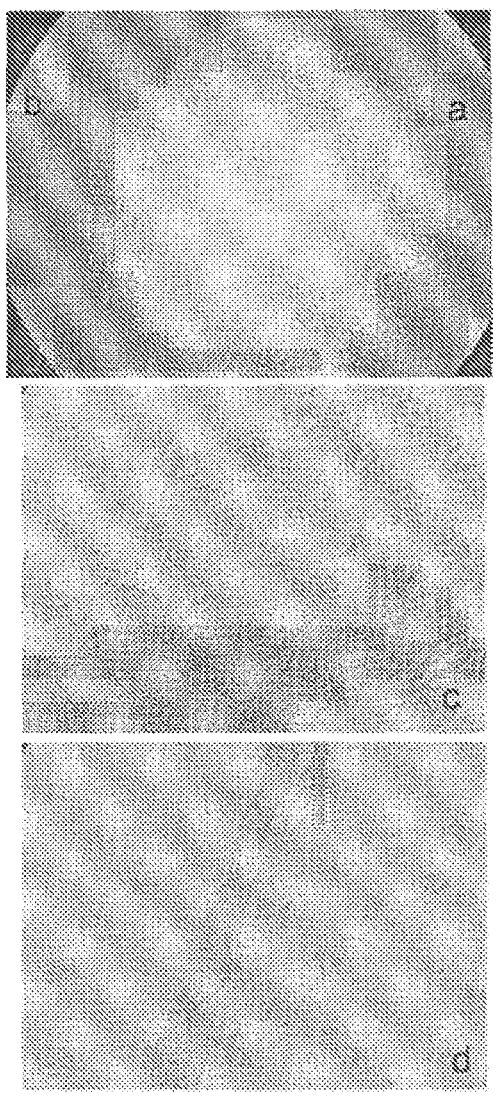
FIG. 24 A series of photographs showing the results of performing in situ hybridization to hsa-miR-196a using a specimen obtained by formalin-fixing and paraffin-embedding the isolated larynx of a progressive laryngeal cancer patient.
Figure 25:
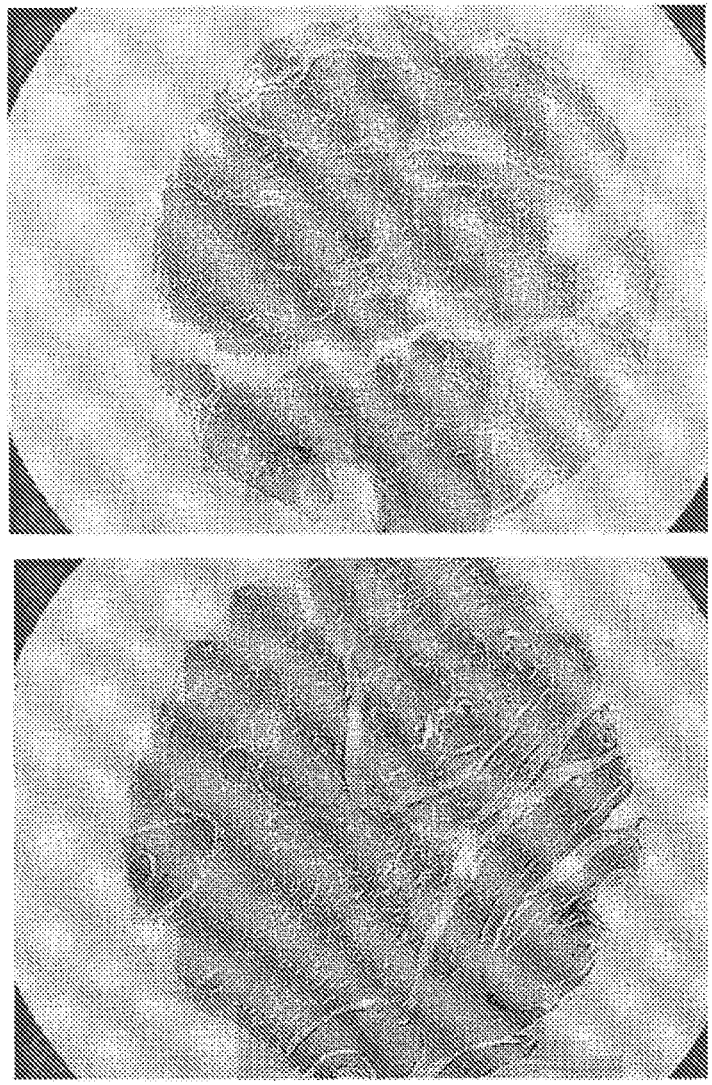
FIG. 25 A set of photographs showing the results of performing in situ hybridization to hsa-miR-196a using laryngeal cancer specimens of Westerners (specimens obtained by formalin-fixing and paraffin-embedding the isolated larynx of Western patients with progressive laryngeal cancer).

The results of FIGS. 24 and 25 can be said to be data strongly suggesting that a microRNA showing tumor-specific expression can be stably detected even in a formalin-fixed tissue and that the disease- and tissue-specific expression signature of a microRNA is conserved beyond the human race.

The above results suggest that a disease-specifically expressed microRNA can be rapidly detected and diagnosed in a tissue using a microRNA detection probe labeled with DIG, a fluorescent label, or the like. The detection, if becoming feasible, can probably be applied to the decision of a resection stump during the surgery of a malignant tumor, the treatment strategy of deciding the range of lymph node dissection by determining the presence of metastasis in the so-called sentinel lymph node, and the like. In addition, the same microRNA detection also has a possibility of providing a useful tool for the diagnosis in a paraffin-embedded biopsied tissue or a surgically excised specimen, diagnosis of the grades of atypism and malignancy of tumorous lesions typified by leukoplakia of the head and neck previously been forced to depend on the subjectivity of a pathologist, or the cytodiagnosis of lymph nodes suspected of tumor invasion or metastasis requiring accurate diagnosis from a few cells, or the like.

The invention claimed is:

1. A method for the detection of a head-and-neck tumor in a subject undergoing testing for head-and-neck tumor, the method comprising the steps of:
   (A) extracting RNA from a clinical specimen tissue from the head and neck of the subject;
   (B) measuring the expression level of miR-196a in the extracted RNA;
   (C) comparing the measured expression level of miR-196a in (B) to the expression level of miR-196a in a control specimen of normal tissue of the same type as that of the clinical specimen tissue; and
   (D) detecting a head-and-neck tumor when the expression level of miR-196a in the extracted RNA is increased compared to the control.

2. The method for the detection of head-and-neck tumor according to claim 1, wherein miR-196a consists of an RNA in which 1 to 5 nucleotides are deleted, substituted, or added in the nucleotide sequence of SEQ ID NO: 6.

3. The method for the detection of head-and-neck tumor according to claim 1, wherein the head-and-neck tumor is laryngeal cancer or squamous cell cancer.

4. The method for the detection of head-and-neck tumor according to claim 1, comprising using, when measuring the expression level of milt-196a, a microarray which includes a polynucleotide consisting of a nucleic acid sequence complementary to the sequence of miR-196a, or a part thereof, and which is capable of measuring the expression level of miR-196a.

5. The method for the detection of head-and-neck tumor according to claim 1, comprising using, when measuring the expression level of milt-196a, a primer set capable of amplifying the sequence of miR-196a and a fluorescent probe comprising a polynucleotide consisting of a nucleic acid sequence complementary to miR-196a, or a part thereof.

* * * * *

```
SEQUENCE LISTING

<160> NUMBER OF SEQ ID NOS: 33

<210> SEQ ID NO 1
<211> LENGTH: 21
<212> TYPE: RNA
<213> ORGANISM: Homo sapiens

<400> SEQUENCE: 1
gcaguccaug ggcauauaca c                                               21

<210> SEQ ID NO 2
<211> LENGTH: 22
<212> TYPE: RNA
<213> ORGANISM: Homo sapiens

<400> SEQUENCE: 2
uaugugccuu uggacuacau cg                                              22

<210> SEQ ID NO 3
<211> LENGTH: 22
<212> TYPE: RNA
<213> ORGANISM: Homo sapiens

<400> SEQUENCE: 3
cagugcaaug augaaagggc au                                              22

<210> SEQ ID NO 4
<211> LENGTH: 21
<212> TYPE: RNA
<213> ORGANISM: Homo sapiens

<400> SEQUENCE: 4
acucuuuccc uguugcacua c                                               21

<210> SEQ ID NO 5
<211> LENGTH: 24
<212> TYPE: RNA
```

-continued

<213> ORGANISM: Homo sapiens

<400> SEQUENCE: 5
gauugcucug cgugcggaau cgac                                          24

<210> SEQ ID NO 6
<211> LENGTH: 21
<212> TYPE: RNA
<213> ORGANISM: Homo sapiens

<400> SEQUENCE: 6
uagguaguuu cauguuguug g                                             21

<210> SEQ ID NO 7
<211> LENGTH: 22
<212> TYPE: RNA
<213> ORGANISM: Homo sapiens

<400> SEQUENCE: 7
uagcuuauca gacugauguu ga                                            22

<210> SEQ ID NO 8
<211> LENGTH: 21
<212> TYPE: RNA
<213> ORGANISM: Homo sapiens

<400> SEQUENCE: 8
ggcaagaugc uggcauagcu g                                             21

<210> SEQ ID NO 9
<211> LENGTH: 21
<212> TYPE: RNA
<213> ORGANISM: Homo sapiens

<400> SEQUENCE: 9
uugguccccu ucaaccagcu a                                             21

<210> SEQ ID NO 10
<211> LENGTH: 23
<212> TYPE: RNA
<213> ORGANISM: Homo sapiens

<400> SEQUENCE: 10
guccaguuuu cccaggaauc ccu                                           23

<210> SEQ ID NO 11
<211> LENGTH: 22
<212> TYPE: RNA
<213> ORGANISM: Homo sapiens

<400> SEQUENCE: 11
uuuguucguu cggcucgcgu ga                                            22

<210> SEQ ID NO 12
<211> LENGTH: 22
<212> TYPE: RNA
<213> ORGANISM: Homo sapiens

<400> SEQUENCE: 12
ugagguagua gguuguauag uu                                            22

<210> SEQ ID NO 13
<211> LENGTH: 22
<212> TYPE: RNA

<213> ORGANISM: Homo sapiens

<400> SEQUENCE: 13
ugagguagua gguugugugg uu                                          22

<210> SEQ ID NO 14
<211> LENGTH: 22
<212> TYPE: RNA
<213> ORGANISM: Homo sapiens

<400> SEQUENCE: 14
ugagguagua gguuguaugg uu                                          22

<210> SEQ ID NO 15
<211> LENGTH: 21
<212> TYPE: RNA
<213> ORGANISM: Homo sapiens

<400> SEQUENCE: 15
agagguagua gguugcauag u                                           21

<210> SEQ ID NO 16
<211> LENGTH: 21
<212> TYPE: RNA
<213> ORGANISM: Homo sapiens

<400> SEQUENCE: 16
ugagguagga gguuguauag u                                           21

<210> SEQ ID NO 17
<211> LENGTH: 22
<212> TYPE: RNA
<213> ORGANISM: Homo sapiens

<400> SEQUENCE: 17
ugagguagua gauuguauag uu                                          22

<210> SEQ ID NO 18
<211> LENGTH: 21
<212> TYPE: RNA
<213> ORGANISM: Homo sapiens

<400> SEQUENCE: 18
ugagguagua guuguacag u                                            21

<210> SEQ ID NO 19
<211> LENGTH: 21
<212> TYPE: RNA
<213> ORGANISM: Homo sapiens

<400> SEQUENCE: 19
ugagguagua guugugcug u                                            21

<210> SEQ ID NO 20
<211> LENGTH: 23
<212> TYPE: RNA
<213> ORGANISM: Homo sapiens

<400> SEQUENCE: 20
caaagugcuu acagugcagg uag                                         23

<210> SEQ ID NO 21
<211> LENGTH: 22
<212> TYPE: RNA

```
<213> ORGANISM: Homo sapiens

<400> SEQUENCE: 21
uaaggugcau cuagugcaga ua                                              22

<210> SEQ ID NO 22
<211> LENGTH: 23
<212> TYPE: RNA
<213> ORGANISM: Homo sapiens

<400> SEQUENCE: 22
ugugcaaauc uaugcaaaac uga                                             23

<210> SEQ ID NO 23
<211> LENGTH: 23
<212> TYPE: RNA
<213> ORGANISM: Homo sapiens

<400> SEQUENCE: 23
ugugcaaauc caugcaaaac uga                                             23

<210> SEQ ID NO 24
<211> LENGTH: 23
<212> TYPE: RNA
<213> ORGANISM: Homo sapiens

<400> SEQUENCE: 24
uaaagugcuu auagugcagg uag                                             23

<210> SEQ ID NO 25
<211> LENGTH: 22
<212> TYPE: RNA
<213> ORGANISM: Homo sapiens

<400> SEQUENCE: 25
uauugcacuu gucccggccu gu                                              22

<210> SEQ ID NO 26
<211> LENGTH: 22
<212> TYPE: RNA
<213> ORGANISM: Homo sapiens

<400> SEQUENCE: 26
uagcagcaca uaaugguuug ug                                              22

<210> SEQ ID NO 27
<211> LENGTH: 22
<212> TYPE: RNA
<213> ORGANISM: Homo sapiens

<400> SEQUENCE: 27
uagcagcaca ucaugguuua ca                                              22

<210> SEQ ID NO 28
<211> LENGTH: 22
<212> TYPE: RNA
<213> ORGANISM: Homo sapiens

<400> SEQUENCE: 28
uagcagcacg uaaauauugg cg                                              22

<210> SEQ ID NO 29
<211> LENGTH: 24
<212> TYPE: RNA
```

```
<213> ORGANISM: Mus musculus

<400> SEQUENCE: 29
augcagucca cgggcauaua cacu                                      24

<210> SEQ ID NO 30
<211> LENGTH: 22
<212> TYPE: RNA
<213> ORGANISM: Mus musculus

<400> SEQUENCE: 30 acucuuccc uguugcacua cu                                         22

<210> SEQ ID NO 31
<211> LENGTH: 24
<212> TYPE: RNA
<213> ORGANISM: Mus musculus

<400> SEQUENCE: 31
gauugcugug cgugcggaau cgac                                      24

<210> SEQ ID NO 32
<211> LENGTH: 22
<212> TYPE: RNA
<213> ORGANISM: Mus musculus

<400> SEQUENCE: 32
ucggcaacaa gaaacugccu ga                                        22

<210> SEQ ID NO 33
<211> LENGTH: 22
<212> TYPE: RNA
<213> ORGANISM: Mus musculus

<400> SEQUENCE: 33
aggcaagaug cuggcauagc ug                                        22
```